(12) United States Patent
Abraham et al.

(10) Patent No.: US 6,486,342 B1
(45) Date of Patent: Nov. 26, 2002

(54) SUBSTITUTED CHIRAL ALLOSTERIC HEMOGLOBIN MODIFIERS

(75) Inventors: Donald J. Abraham, Midlothian, VA (US); Gajanan S. Joshi, Glen Allen, VA (US); Stephen J. Hoffman, Carlisle, MA (US); Melissa Grella, Columbia, MD (US); Richmond Danso-Danquah, Richmond, VA (US); Amal Yousseff, Richmond, VA (US); Martin Safo, Richmond, VA (US); Sanjeev Kulkarni, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/643,874

(22) Filed: Aug. 23, 2000

Related U.S. Application Data

(60) Provisional application No. 60/150,351, filed on Aug. 24, 1999, and provisional application No. 60/176,635, filed on Jan. 19, 2000.

(51) Int. Cl.$^7$ .................. C07C 261/00; C07C 69/76; C07C 229/00; C07C 62/38
(52) U.S. Cl. ............... 560/30; 560/8; 560/19; 560/31; 560/32; 560/400; 514/563
(58) Field of Search ................ 560/8, 19, 32, 560/30, 31, 400; 514/563

(56) References Cited

U.S. PATENT DOCUMENTS 5,122,539 A  *  6/1992  Abraham et al. ........... 514/563

* cited by examiner

*Primary Examiner*—Alan L. Rotman
*Assistant Examiner*—Hector M Reyes
(74) *Attorney, Agent, or Firm*—Whitham, Curtis & Christofferson, P.C.

(57) ABSTRACT

A family of substituted chiral allosteric effectors of hemoglobin is useful for delivering more oxygen to hypoxic and ischemic tissues by reducing the oxygen affinity of hemoglobin in whole blood.

16 Claims, No Drawings

SUBSTITUTED CHIRAL ALLOSTERIC HEMOGLOBIN MODIFIERS

This application is based on U.S. Prov. App. No. 60/150,351, filed on Aug. 24, 1999 and No. 60/176,635 filed Jan. 19, 2000, incorporated by reference in its entirety.

DESCRIPTION

BACKGROUND OF THE INVENTION

1. Field of the Invention

The present invention generally relates to a family of allosteric effectors of hemoglobin and more specifically to chirality affects of allosteric effectors where the chiral carbon has a substituted carbon ring, a heteroatom ring, or different substituents. The invention includes several new potent enantiomers that are superior than their racemic mixture and other enantiomeric isomer, possessing different degrees of allosteric potency.

2. Background Description

Human hemoglobin (Hb) is a tetrameric allosteric protein comprised of two alpha and two beta chains and functions to deliver oxygen from the lungs to the many tissues of the body. The four subunits are arranged around a molecular two fold axis creating a central water cavity. As an allosteric protein, Hb exists in an equilibrium between two states, the relaxed (R) or oxy-state and the tense (T) or deoxy-state. In the oxy-state, the water cavity is narrow and the subunits have fewer and weaker bonds between them (i.e., relaxed). However, in the deoxy-state, the water cavity is larger, and the subunits are tightly tethered together by salt bridges (i.e., tense). The allosteric equilibrium can be influenced by allosteric modifiers. Such molecules can increase the oxygen affinity of Hb shifting the allosteric equilibrium toward oxy-Hb or decrease the affinity of oxygen, shifting the equilibrium to the deoxy-Hb. Modifiers that decrease the oxygen affinity act by adding constraints to the T-state. Oxygen affinity decreasing agents have several potential applications including radiosensitization of tumors, enhancement of oxygen delivery to hypoxic and ischemic tissues, and shelf-life prolongation of stored blood.

The gap between the β subunits is wide enough for 2,3-diphosphoglycerate (2,3-DPG), a naturally occuring allosteric modifier, to dock in and bind, forming additional salt bridges that further stabilize the deoxy state. Therefore, compounds that lower the affinity of oxygen for Hb do so by strengthening the existing salt bridges or by adding new ones to the tense state.

Several synthetic agents have been reported to lower the affinity of oxygen for Hb. In the search for an antisickling agent, Abraham and coworkers discovered the antilipidemic drug, clofibric acid, that lowered the oxygen affinity of Hb. Perutz and Poyart followed with a report that bezafibrate, another antilipidemic agent, was also a right-shifting compound, more potent than DPG and clofibric acid. Lalezari and coworkers demonstrated that shortening the four atom bridge to a three atom urea bridge produced even more potent allosteric modifiers, but their potential as clinical agents was limited due to loss of activity in the presence of serum albumin.

It has been proposed that influencing the allosteric equilibrium of hemogobin is a viable avenue of attack for treating diseases. The conversion of hemoglobin to a low affinity state is believed to have general utility in a variety of disease states where tissues suffer from low oxygen tension, such as ischemia and radio sensitization of tumors. Several synthetic compounds have been identified which have utility in the allosteric regulation of hemoglobin and other proteins.

SUMMARY OF THE INVENTION

It is therefore an object of the present invention to provide a family of compounds which allosterically modifies hemoglobin such that hemoglobin is present in blood in a lower oxygen affinity state.

It is therefore an object of the present invention to provide synthetic agents that can enhance the oxygenation of tissues. Enhancement of oxygenation has several potential therapeutic applications: (1) radio-sensitization of tumors, (2) treatment of stroke and cerebral traumas, (3) shelf-life prolongation of stored blood, (4) treatment of angina and myocardial infarcation, and (5) reduction of surgical blood loss and blood transfusions.

Currently, two of the most potent oxygen-affinity decreasing agents developed by Abraham et al. are shown as RSR13 and JP7 in Table I below. The high resolution crystal structure of the RSR13-Hb complex has been determined. The small molecule binds near the top of the α subunits and points down the central water cavity to the α,β-subunit interfaces making several important interactions with the protein. RSR46, KDD86, and RSR4 shown in Table I are also oxygen affinity decreasing agents.

TABLE I

| Name | Compound |
|---|---|
| 1 RSR13 | 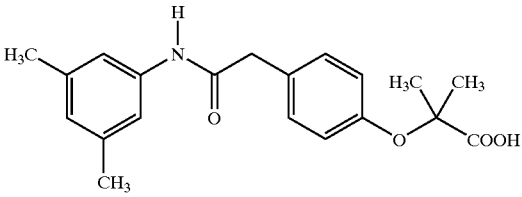 |

TABLE I-continued

| Name | Compound |
|---|---|
| 2 JP7 | 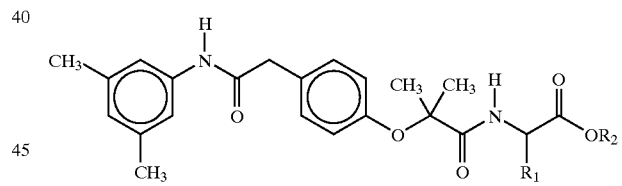 |
| 3 RSR46 | |
| 4 RSR4 | |
| 5 KDD86 | |

Specifically, compounds having substituted chiral centers and the structures:

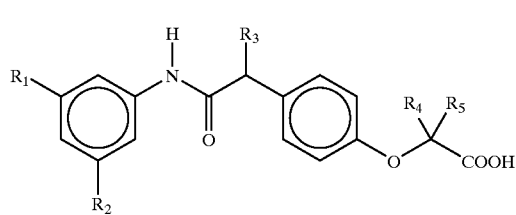

A wherein $R_1$ and $R_2$ are selected from the group comprising $CH_3$, Cl, and 5 carbon cyclics; $R_3$ is selected from the group comprising H, OH, and $OC_2H_5$; $R_4$ and $R_5$ are selected from the group comprising $CH_3$, cyclics containing $CH_3$ substituents, $OCH_3$, $C_2H_5$, phenyl and substituted phenyl; and wherein $R_4$ and $R_5$ are not the same, and

B wherein $R_1$ is selected from the group comprising H, $CH_3$, $CH(CH_3)_2$, $CH_2Ph$, $CH_2CH(CH_3)_2$, $CH(CH_3)C_2H_5$, $CH_2CH_2COOH$, $CH_2COOH$, $CH_2$tryptophan, $CH_2$ Indole, $CH_2PhOH$, $CH_2OH$, $CH_2SCH_3$, $(Me)_2SMe$, $(CH_2)_3$, $CH_2SCH_2Ph$, $CH(OH)CH_3$, $(CH_2)_4NHOCOCH_2Ph$, and $(CH_2)_4NH_2$.

C

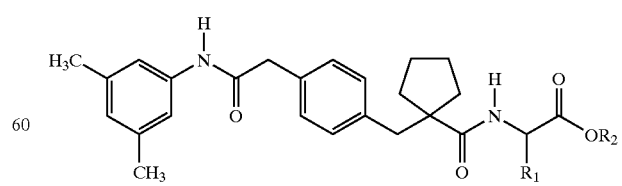

Where $R_3$ is selected from the group comprising H, $CH_3$, $CH(CH_3)_2$, $CH_2Ph$, $CH_2CH(CH_3)_2$, $CH(CH_3)C_2H_5$, $CH_2CH_2COOH$, $CH_2COOH$, $CH_2$tryptophan, $CH_2$ Indole, $CH_2PhOH$, $CH_2OH$, $CH_2SCH_3$, $(Me)_2SMe$, $(CH_2)_3$, CH$_2$SCH$_2$Ph, CH(OH)CH$_3$, (CH$_2$)$_4$NHOCOCH$_2$Ph, (CH$_2$)$_4$NH$_2$ etc. have been identified as being allosteric effectors of hemoglobin.

Investigation of the effect of stereochemistry on activity and binding conformation shows that the existence of a chiral center affects the allosteric activity. Specifically, a chiral center was introduced in compounds having the general structures of RSR13, JP7, RSR4, RSR46 and KDD86 (shown in Table I). The new chiral molecules (class B) were prepared by replacing either one of the gem dimethyl groups of Table I compounds with other alkyl/alkanoic, un/substituted cycloalkyl/cycloalkanoic, substituted aromaatic groups or by condensing the carboxylate group of the parent.molecule (Table 1 compounds) with various D and L isomers of amino acids such as alanine, valine, asparagine, cysteine, glutamic acid, phenylalanine, glycine, histidine, leucine, isoleucine, proline, arginine, serine, threonine, tryptophan, tyrosine, and lysine (class C).

The synthesis of the compounds (class B) involves central intermediate amidophenols: 4-[[(3,5-dimethylanilino)carbonyl]methyl]phenol, 4-[[(5-indanyl)carbonyl]methyl]phenol, and 4-[[(3-chloro-5-methylanilino)carbonyl]methyl]phenol, where 3,5 dimethylaniline or 5-aminoindan is condensed with 4-hydroxyphenylacetic acid in refluxing xylene over a three-day period. While 3,5-dimethylaniline and 5-aminoindan were both readily available.

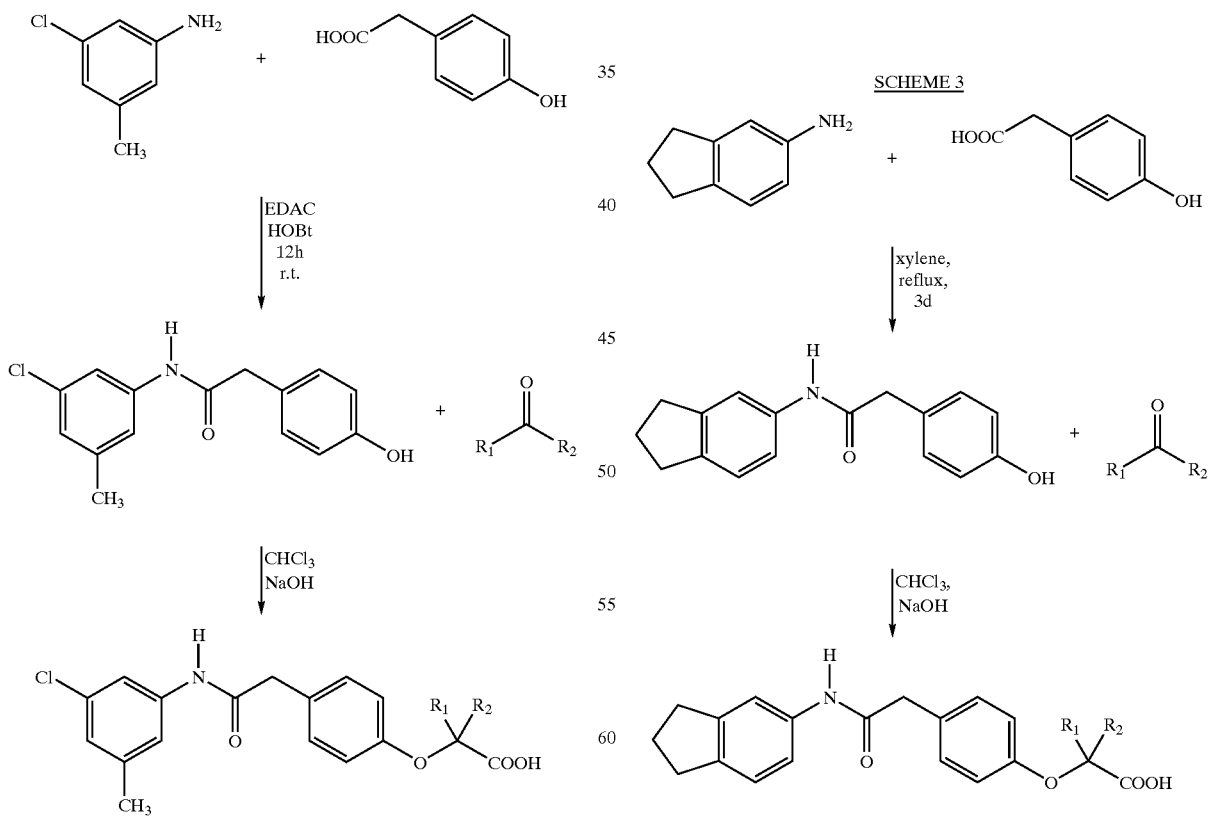

The scheme 1 above as well the schemes 2 and 3 shown below were utilized to produce the corresponding racemates.

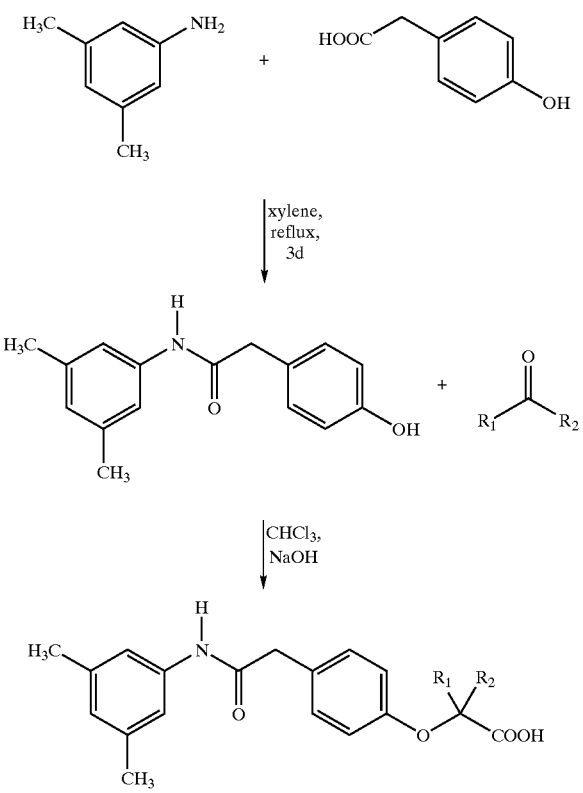

The previously reported α-aryloxyisobutyric acid analogs were obtained via reaction of amidophenols with acetone-chloroform in the presence of sodium hydroxide. In this process, the appropriate ketone is substituted for acetone in tetrahydrofuran to obtain the proposed compounds 1-[4-[[(3,5-dimethylanilino)carbonyl]methyl]phenoxy]-3-methylcyclopentane carboxylic acid, 2-[4-[[(3,5-dimethylanilino)carbonyl]methyl]phenoxy-2-methylbutanoic acid 1-4-[[(3,5-dimethylanilino)carbonyl]methyl]phenoxy]-2-methylcyclopentane carboxylic acid, 4-[4-[[(3,5-dimethylanilino)carbonyl]methyl]phenoxy]tetrahydro-2H-4-pyrancarboxylic acid, 3-[4-[[(3,5-dimethylanilino)carbonyl]methyl]phenoxy]-2-methyltretrahydro-3-furan carboxylic acid, 2-[4-[[(3,5-dimethylanilino)carbonyl]methyl]phenoxy]-3-methoxy-2-methylpropanoic acid, 2-[4-[[(3,5-dimethylanilino)carbonyl]methyl]phenoxy]-2-methylpentanoic acid, 1-[4-[[(3,5-dimethylanilino)carbonyl]methyl]phenoxy]-3-methylcyclohexane carboxylic acid, 1-[4-[[(5-indanyl)carbonyl]methyl]phenoxy]-3-methyl cyclopentane carboxylic acid, 2-[4-[[(5-indanyl)carbonyl]methyl]phenoxy]-2-methylbutanoic acid, 2-[4-[[(5-indanyl)carbonyl]methyl]phenoxy]-2-methylcyclopentane carboxylic acid, 1-[4-[[(3-chloro-5-methylanalino)carbonyl]methyl]phenoxy]-3-methylcyclopentane carboxylic acid, 2-[4-[[(3-chloro-5-methylanalino)carbonyl]methyl]phenoxy]-2-butanoic acid, 1-[4-[[(3-chloro-5-methylanalino)carbonyl]methyl]phenoxy]-2-methylcyclopentane carboxylic acid.

The schemes 4 and 5 were used to prepare racemates of the compounds 2-[4-[[(3,5-dimethylanilino)carbonyl]methyl]phenoxy]-proprionic acid, 2-[4-[[(3,5-dimethylanilino)carbonyl]methyl]phenoxy]-2-fluoroacetic acid, 2-[4-[[(3,5-dimethylanilino)carbonyl]methyl]phenoxy]-butanoic acid, 2-[4-[[(3,5-dimethylanilino)carbonyl]methyl]phenoxy]-pentanoic acid, 2-[4-[[(3,5-dimethylanilino)cardonyl]methyl]phenoxy]-hexanoic acid, 2-[4-[[(3-chloro-5-methylanilino)carbonyl]methyl]phenoxy]-propionic acid, 2-[4-[[(3-chloro-5-methylanilino)carbonyl]methyl]phenoxy]-butanoic acid, 2-[4-[[(5-indanyl)carbonyl]methyl]phenoxy]-propionic acid, and 2-[4-[[(5-indanyl)carbonyl]methyl]phenoxy]-butanoic acid.

SCHEME 4

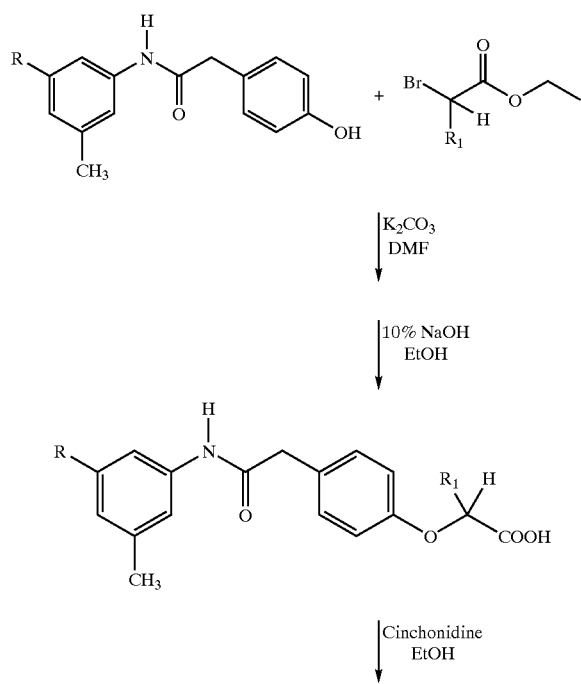

SCHEME 5

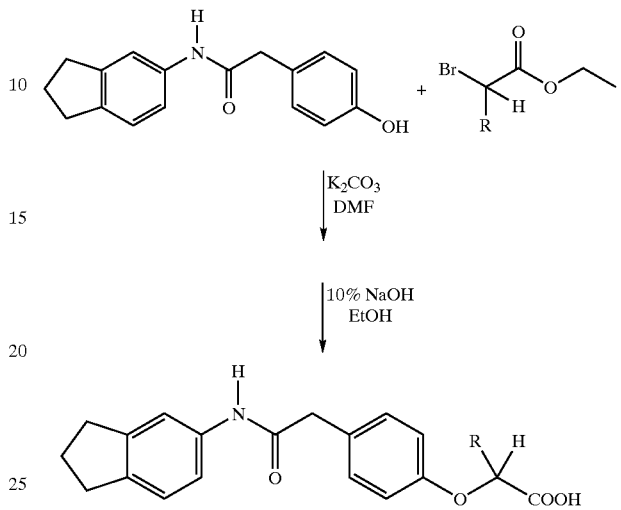

This method employs condensation of the corresponding amidophenol with the α-bromo ester in the presence of base followed by base hydrolysis of the ester to give the desired α-aryloxy acid product.

DETAILED DESCRIPTION OF A PREFERRED EMBODIMENT OF THE INVENTION

Abraham et al. designed and synthesized a series of fibrate analogs that replaced the urea bridge with an amide bridge and modified the substitution on ring A. Compounds from the series exhibited greater allosteric activity than benzafibrate. The most potent derivatives from the series were RSR4 and RSR13, as shown in Table 1 above.

X-ray crystallography studies of bezafibrate complexed with Hb showed that two symmetrically related molecules bind near the top of the α subunits and point down the central water cavity to the α,β-subunit interfaces making several important interactions with the protein. The high resolution x-ray crystal structure of the RSR13-Hb complex showed that the molecule binds similarly to bezafibrate. The carboxylic acid group of RSR13 forms a water-mediated salt bridge with Arg 141α, the amide oxygen makes a hydrogen bond with Lys 99α and the gem dimethyl group lies in a hydrophobic pocket lined with residues Pro 95α, Tyr 140α, and Trp 37β.

The present invention was designed to investigate the effect of chirality on the allosteric activity of a series of modifiers and determine their effect on binding mode with Hb. This invention describes the synthesis of several chiral allosteric modifiers of Hb which replaced the gem dimethyl group with alkyl groups, substituted, cycloalkyl groups, and cycloalkyl groups with heteroatoms in the ring. The compounds were based on the ring A templates of RSR13, RSR46, JP7, RSR4 and KDD86. In addition, the structure of JP7 was also modified by adding-substituents to the cyclopentyl ring to give substituted chiral derivatives. Select compounds from the RSR13 and JP7 series were resolved into the enantiomers to determine the effect of the stereocenter on activity. Molecule selection for separation was based on degree of activity and substitution pattern. To formulate SAR, the prepared derivatives were analyzed with Hb solution. In vitro testing with whole blood was also conducted. From studying the binding site of RSR13 and the position of the gem dimethyl group, it was anticipated that one of the enantiomers will bind differently to the hydrophobic pocket and therefore have different effects on the allosteric equilibrium.

All reagent and starting material used in the syntheses were purchased from Aldrich, Fluka, or Sigma and used without purification. All solvents were purchased form Aldrich or Fisher. Silica gel coated plates (0.25 mm thickness) from Analtech, Inc. were used for thin layer chromatography (TLC). Separations were visualized by ultraviolet (UV) lamp or by iodine exposure. Column chromatography was performed on silica gel (Merc, grade 9385, 230–400 mesh). Melting points (mp) were determined on a Thomas-Hoover melting point apparatus and were uncorrected. Proton nuclear magnetic resonance (H NMR) spectra were obtained on a Varian Gemini 300 MHz Spectrophotometer and are reported in parts per million (δ ppm) with tetramethylsilane as the internal standard. Elemental analyses were performed by Atlantic Microlab, Inc. (Norcross, Ga.) and results are within ±4% of the theoretical value. All intermediate compounds were analyzed but are not reported. Their purity was determined by TLC and $^1$H NMR.

EXAMPLE 1

Scheme 2 Illustrates a Reaction Scheme for Preparing 4-[[(3,5-dimethylanilino)carbonyl]methyl] phenol, a Compound That Is Useful as a Precursor in the Preparation of Some of the Table II Compounds A mixture of 4-hydroxyphenylacetic acid (20.0 g, 131 mmol) and 3,5-dimethylaniline (15.9 g, 131 mmol) in xylene (100 mL) was stirred for three days at 160° C. with a Dean Stark trap. The mixture was cooled to room temperature and filtered. The solid product obtained was washed with hexane (200 mL), 10% sodium bicarbonate solution (250 mL), water (200 mL), 10% hydrochloric acid (200 mL), and then water (200 mL). The beige solid was air dried to yield 27.7 g, 82.7%. mp 183–185° C.
$^1$H NMR (CDCl$_3$): δ2.25 (s,6H), 3.60(s,2H), 6.71(s,1H), 6.82(d,2H,J=8.5 Hz), 7.05 (s,2H), 7.13 (d, 2H, J=8.4 Hz).
Anal: C$_{16}$H$_{17}$NO$_2$; Calculated C 75.27, H 6.71, N 5.49; Found C 75.18, H 6.69 and N 5.36

1-[4-[[(3,5-dimethylanilino)carbonyl]phenoxy]-3-methylcyclopentane carboxylic acid (3)

Sodium hydroxide (1.8 g, 45 mmol) was added to a stirred solution of 4-[[(3,5-dimethylanilino)carbonyl]methyl] phenol (1.27 g, 5 mmol) in anhydrous tetrahydrofuran (30 mL). After 15 min, 3-methylcyclopentanone (4.9 g, 50 mmol) was added dropwise. The reaction mixture was maintained at 0° C. for 2 h and then allowed to come to room temperature while stirring overnight. Tetrahydrofuran was removed under reduced pressure. The residue was dissolved in water (150 mL) and washed with ethyl acetate (2×30 mL). The aqueous layer was acidified (pH2) with concentrated HCl and extracted with ethyl acetate (3×40 mL). The combined organic fractions were washed with brine, dried over anhydrous MgSO$_4$, and the solvent was removed under reduced pressure. The brown oil was purified by flash chromatography (eluent: hexane/ethyl acetate, 2:1) to afford a pale yellow powdery solid, 0.89 g, 47%. mp 148–153° C.
$^1$H NMR (CDCl$_3$): δ1.03 (d,3H,J=6.6 Hz), 1.27–2.31 (m,6H), 2.24(s,6H), 2.40–2.66(m,1H), 3.60 (s,2H), 6.73 (s,1H), 6.78 (d,2H,J=8.5 Hz), 7.06(s,2H), 7.18 (d,2H,J=8.4 Hz).

Anal: C$_{23}$H$_{27}$NO$_4$.0.25H$_2$O; Calculated C 71.57, H,7.18, N 3.63; found C 71.76, H 7.17 and N 3.53

Compounds 1–4, 6, 10 and 11 were prepared using the same procedure as described above for 3.

1-[4-[[(3,5-dimethylanilino)carbonyl]methyl] phenoxyl-2-methylcyclopentane carboxylic acid (1)

2-Methylcyclopentanone (3.46 g, 35.3 mmol) and 4-[[(3,5-dimethylanilino)carbonyl]methyl]phenol (1.0 g, 3.9 mmol) were reacted to yield a brown oil. The oil was purified by flash chromatography (eluent: hexane/ethyl acetate 3:1) to give a yellow solid. Recrystallization from methylene chloride and hexane gave a white solid, 0.30 g, 20%. mp 184–186° C.
$^1$H NMR (CD$_3$OD): δ1.02 (d,3H,J=7.2 Hz), 1.43–2.46 (m,6H), 2.25 (s,6H), 2.48–2.54 (m,1H), 3.56 (s,2H), 6.53 (s,1H), 6.55 (d,2H,J=8.3 Hz), 6.94 (s,2H), 7.00 (d,2H,J=8.4 Hz).
Anal: C$_{23}$H$_{27}$NO$_4$.0.25H$_2$O; Calculated C 71.57, H 7.18, N 3.63; found C 71.54, H7.15 and N 3.50

4-[4-[[(3,5-dimethylanilino)carbonyl]methyl] phenoxy]tetrahydro-2H-4-pyrancarboxylic acid (4)

Tetrahydro-4H-pyran-4-one (4.5 g,45 mmol) and 4-[[(3,5-dimethylanilino)carbonyl]methyl]phenol (1.3 g,5 mmol) were reacted to yield a yellow-brown oil. The product was purified by flash chromatography (eluent: hexane/ethyl acetate, 2:1) to afford a pale yellow solid. Recrystallization with methylene chloride and hexane gave a white solid, 0.85 g, 45%. mp 186–188° C.
$^1$H NMR (CD$_3$OD): δ2.05–2.23 (m, 4H), 2.29 (s,6H), 3.63 (s,2H), 3.79 (m,4H), 6.79 (s,1H), 6.92 (d,2H,J=8.6 Hz), 7.19 (s,2H), 7.30 (d,2H,J=8.6 Hz).
Anal: C$_{22}$H$_{25}$NO$_5$.0.25H$_2$O; Calculated C 68.11, H 6.63, N 3.61; found C 67.90, H 6.66, N 3.60.

3-[4-[[(3,5-dimethylanifino)carbonyl]methyl] phenoxy]-2-methyltetrahydro-3-furan carboxylic acid (2)

2-Methyltetrahydrofuran-3-one (3.5 g,35 mmol) and 4-[[(3,5-dimethylanilino)carbonyl]methyl]phenol (1.0 g,3.9 mmol) were reacted to give an orange oil. Purification by column chromatography (eluent: hexane/ethyl acetate 3:1–1:2) afforded a yellow oil which upon recrystallization from methylene chloride and hexane gave a white solid, 0.47 g, 32%. mp 187–190° C.
$^1$H NMR (DMSO-d6): δ1.16 (d,3H,J=6.5 Hz), 2.15 (m,1H), 2.21 (s,6H), 2.75 (m,1H), 3.51 (s,2H), 3.73 (q,1H, J=7.5 Hz), 3.97–4.14 (m,2H), 6.67 (s,1H), 6.71 (d,2H,J=8.6 Hz), 7.20 (s,2H), 7.22 (d,2H,J=8.3 Hz).
Anal: C$_{22}$H$_{25}$NO$_5$; Calculated C 68.91, H 6.57, N 3.65; found C 68.79, H 6.56, N 3.59

2-[4-[[(3,5-dimethylanilino)carbonyl]methyl] phenoxy]-3-methoxy-2-methylpropanoic acid (10)

Methoxyacetone (10.0 g, 113 mmol) and 4-[[(3,5-dimethylanilino)carbonyl]methyl]phenol (3.22 g,12.6 mmol) were reacted together as described for compound 9 to yield an orange-brown semisolid. The product was recrystallized from methylene chloride and hexane to give a pale yellow solid, 2.27 g, 48%. mp 170–172° C.
$^1$H NMR (CD$_3$OD): δ1.46 (s,3H), 2.25 (s,6H), 3.37 (s,3H), 3.59 (s,2H), 3.66 (s,2H), 6.74 (s,1H), 6.95 (d,2H,J= 8.5 Hz), 7.15 (s,2H), 7.24 (d,2H,J=8.5).

Anal: $C_{21}H_{25}NO_5$; Calculated C 67.91, H 6.78, N 3.77; found C 67.73, H 6.84 and N 3.66

2-[4-[[(3,5-dimethylanilino)carbonyl]methyl]phenoxy]-2-methylpentanoic acid (6)

Using 4-[[(3,5-dimethylanilino)carbonyl]methyl]phenol (1.5 g,5.9 mmol) and 2-pentanone (4.55 g,52.9 mmol), compound 6 was prepared as described for compound 9. The brown semi-solid obtained was purified by flash chromatography (eluent: hexane/ethyl acetate 3:1→1:1). Recrystallization from methylene chloride and hexane gave a white amorphous solid, 0.70 g, 32%. mp 145–147° C.

$^1$H NMR (CD$_3$OD): δ0.94 (t,3H,J=7.3 Hz), 1.46 (s,3H), 1.47 (m,2H), 1.88 (m,2H), 2.25 (s,6H), 3.58 (s,2H), 6.74 (s,1H), 6.87 (d,2H,J=8.6 Hz), 7.15 (s,2H), 7.23 (d,2H,J=8.6 Hz).

Anal: $C_{22}H_{27}NO_4$; Calculated C 71.52, H 7.37, N 3.79; found C 71.49, H 7.41 and N 3.76

1-[4-[[(3,5-dimethylanilino)carbonyl]methyl]phenoxyl-3-methylcyclohexane carboxylic acid (11)

3-Methylcyclohexanone (4.39 g,39.2 mmol) and 4-[[(3,5-dimethylanilino)carbonyl]methyl]phenol (1.0 g,3.9 mmol) were reacted together to give a light brown oil. The product was purified by flash chromatography (eluent: hexane/ethyl acetate 2:1), followed by recrystallization from methylene chloride and hexane to obtain white fluffy crystals, 0.08 g, 5%. mp 175–177° C.

$^1$H NMR (CD$_3$OD): δ0.93 (d,3H), J=6.3 Hz), 1.20 (m,1H), 1.45–1.80 and 2.37 (m,8H), 2.26 (s, 6H), 3.58 (s, 2H), 6.75 (s, 1H), 6.90 (d, 2H, J=8.6 Hz), 7.15 (s,2H), 7.22 (d,2H,J=8.6 Hz).

Anal: $C_{24}H_{29}NO_4$; Calculated C 72.89, H 7.39, N 3.54; found C 73.07, H 7.41 and N 3.44.

Scheme 4 Illustartes a General Reaction Scheme for Preparing 4-[[(5-indanyl)carbonyl]methyl]phenol, an Intermediate in the Preparation of Some of the Table 1 Compounds Using 5-aminoindan (10.0 g,75.2 mmol) and 4-hydroxyphenylacetic acid, the amide was synthesized as described for 4-[[(3,5-dimethylanilino)carbonyl]methyl]phenol to give a brown solid, 18.1 g, 90%. mp 148–150° C.

$^1$H NMR (CDCl$_3$): δ2.04 (m,2H), 2.84 (m,4H), 3.60 (s,2H), 6.83 (d,2H,J=8.5 Hz), 7.13 (s,2H), 7.15 (d,2H,J=8.5 Hz), 7.35 (s,1H).

Compounds 5 and 7 were prepared using the same procedure as described above for compound 3.

1-[4-[[(5-indanyl)carbonyl]methyl]phenoxy]-3-methyl cyclopentane carboxylic acid (5)

3-Methylcyclopentanone (5.9 g,60 mmol) and above amidophenol (1.6 g,6.0 mmol) were reacted to yield a brown oil. Purification by flash chromatography (eluent: hexane/ethyl acetate 2:1) afforded a yellow oil. Recrystallization with ether and hexane gave yellow crystals, 0.87 g, 37%. mp 148–151° C.

$^1$H NMR (CD$_3$OD): δ1.06 (d,3H,J=6.6 Hz), 1.32–2.32(m, 6H), 2.05(m,2H), 2.42–2.67(m,1H), 2.84(m,4H), 3.56(s, 2H), 6.78(d,2H, J=8.5 Hz), 7.12(s,2H), 7.20(d,2H,J=8.5 Hz) 7.37(s,1H).

Anal: $C_{24}H_{27}NO_4$; Calculated C 73.26, H 6.92, N 3.56; found C 73.28, H 7.00 and N 3.61

2-[4-[[(5-indanyl)carbonyl]methyl]phenoxyl-2-methylbutanoic acid

2-Butanone (5.4 g, 75 mmol) and above amidophenol (2.0 g, 7.5 mmol) were reacted to yield a brown oil. The product was purified by flash. chromatography (eluent: hexane/ethyl acetate, 2:1) to give a yellow solid. Recrystallization from methylene chloride and hexane afforded a pale yellow solid, 0.85 g, 3 1%. mp 160–161° C.

$^1$H NMR (CDCl$_3$): δ1.01 (t,3H,J=7.5 Hz), 1.49 (s,3H), 1.95(m,2H), 2.04(m,2H), 2.85(m,4H), 3.60(s, 2H), 6.91(d, 2H,J=8.5 Hz), 7.12(s,2H), 7.21(d,2H, J=8.5 Hz), 7.37(s,1H).

Anal. ($C_{22}H_{25}NO_4$); Calculated C 71.91, H 6.86, N 3.56; found C 73.28, H 7.00 and N 3.61

2-[4-[[(5-indanyl)carbonyl]methyl]phenoxyl-2-methylcyclopentane carboxylic acid (7)

2-Methylcyclopentanone (3.30 g,33.7 mmol) and 4-[[(3,5-indanyl)carbonyl]methyl]phenol (1.0 g, 3.7 mmol) were reacted together as described for 9. The product was recrystallized from acetone and ether to yield a tan amorphous solid, 0.40 g, 27%. mp. 191–193° C.

$^1$H NMR (CD$_3$OD, free acid): δ1.02(d,3H,J=7.1 Hz), 1.432.46(m,6H,), 2.05(m,2H), 2.48–2.55(m,1H), 2.84(m, 4H), 3.57(s,2H), 6.75(d,2H,J=8.7 Hz), 7.13(s, 2H), 7.22(d, 2H,J=8.7 Hz), 7.41(s, 1H).

Anal. ($C_{24}H_{27}NO_4 \cdot 0.25H_2O$); Calculated C 72.43, H 6.96, N 3.52; found C 72.20, H 7.02 and N 3.77

The synthesis of mixed chloro-methyl substituted compounds was performed as follows:

4-[[(3-chloro-5-methylanilino)carbonyl]methyl]phenol

To a solution of 4 hyroxyphenylacetic acid (5.9 g,39 mmol) and 1-hydroxybenzotriazole hydrate (5.8 g,43 mmol) in dimethylformamide (40 mL), 25 (5.5 g, 39 mmol) and 1-(3-dimethylaminopropyl)-3-ethylcarbodiimide hydrochloride (9.0 g,47 mmol) were added. The reaction mixture was stirred overnight at room temperature, then diluted with ethyl acetate (100 mL). The mixture was washed with water (3×5 mL) and 10% potassium hydrogen sulfate (3×50 mL). The organic layers were combined and washed with brine, then dried over anhydrous MgSO$_4$. The solvent was removed under reduced pressure to give a brown oil. Recrystallization from methylene chloride and hexane afforded a beige solid, 6.26 g, 58%. mp 176–178° C.

$^1$H NMR (CDCl$_3$): δ2.26(s,3H), 3.54(s,2H), 6.74(d,2H, J=8.6 Hz), 6.91 (s,1H), 7.14(d,2H,J=8.6 Hz), 7.23(s,1H), 7.52(s,1H).

Compounds 8 and 9 were prepared using the same procedure as described above for 3.

1-[4-[[(3-chloro-5-methylanilino)carbonyl]methyl]phenoxy]-3-methylcyclopentane carboxylic acid (9)

3-Methylcyclopentanone (3.57 g, 36.4 mmol) and above amidophenol (1.0 g, 3.6 mmol) were reacted together to give a brown oil. The impure product was purified by flash chromatography (eluent: hexane/ethyl acetate 3:1–2:1) to give a yellow semisolid. Recrystallization. from methylene chloride and hexane yielded a white solid, 0.38 g, 26%. mp 164–166° C.

$^1$H NMR (CD$_3$OD): δ1.04(d,3H,J=6.6 Hz), 1.36–2.32(m, 6H), 2.29(s,3H), 2.43–2.67(m,1H), 3.58(s,2H), 6.73(d,2H, J=8.6 Hz), 6.91 (s,1H), 7.20(d,2H,J=8.7 Hz), 7.22(s,1H), 7.51(s,1H).

Anal. ($C_{22}H_{24}ClNO_4$); Calculated C 65.75, H 6.02, Cl 8.82, N 3.49; found C 65.77, H 6.17, Cl 8.72 and N 3.47

2-[4-[[(3-chloro-5-methylanilino)carbonyl]methyl]phenoxyl-2-methylbutanoic acid 2-Butanone (4.64 g,64.4 mmol) and above amidophenol (1.77 g,6.44 mmol) were reacted together to give a brown oil. Purification by flash chromatography (eluent: hexane/ethyl acetate 3:1–2:1) followed by recrystallization from methylene chloride and hexane afforded a beige solid, 0.44 g, 18%. A small portion of the product was purified for analytical purposes via esterification which was purified by flash chromatography (eluent: hexane/ethyl acetate 4:1) then hydrolyzed to the acid to give white fluffy crystals. mp 101–103° C.

$^1$H NMR (CD$_3$OD): δ0.99 (t,3H,J=7.4 Hz), 1.45(s,3H), 1.96(m,2H), 2.29(s,3H), 3.59(s,2H), 6.87(d,2H,J=8.6 Hz), 6.92(s, 1H), 7.22(d, 2H,J=8.5 Hz), 7.24(s,1H) 7.51(s,1H).

Anal. (C$_{20}$H$_{22}$ClNO$_4$); Calculated C 63.91, H 5.90, Cl 9.43, N 3.73; found C 63.95, H 5.98, Cl 9.33 and N 3.62

1-[4-[[(3-chloro-5-methylanilino)carbonyl]methyl]phenoxyl-2-methycyclopentane carboxylic acid (8)

2-Methylcyclopentanone (3.57 g,36.4 mmol) and above amidophenol (1.0 g, 3.6 mmol) were reacted together to give a brown oil. Purification by flash chromatography (eluent: hexane/ethyl acetate 3:1→2:1) gave a yellow solid. Recrystallization from methylene chloride and hexane yielded a white solid, 0.15 g, 10%. mp 180–182° C.

$^1$H NMR (CD$_3$OD): δ1.02 (d,3H,J=7.1 Hz), 1.43–2.48 (m,6H), 2.52–2.57(m, 1H), 3.58(s,2H), 6.76(d,2H,J=8.6 Hz), 6.92 (s,1H), 7.21 (d,2H,J=8-7 Hz), 7.24(s,1H), 7.52(s, 1H).

Anal. (C$_{22}$H$_{24}$ClNO$_4$·1.0H$_2$O); Calculated C 65.75, H 6.02, Cl 8.82, N 3.49; found C 65.84, H 6.15, Cl 8.75 and N 3.58

2-[4-[[(3,5-dimethylanilino)carbonyl]methyl]phenoxyl-propionic acid (18)

Ethyl 2 bromopropionate (1.8 g,10 mmol) was added to a stirred mixture of 4-[[(3,5-dimtheyanilino)carbonyl]methyl]phenol (1.27 g,5.00 mmol) and potassium carbonate (1.4 g,10 mmol) in dry dimethylformamide (30 mL). The mixture was heated overnight at 80° C., cooled to room temperature, and diluted with ethyl acetate (100 mL). The mixture was washed with water (3×4 mL) followed by brine. The organic layer was dried over anhydrous MgSO$_4$ and concentrated under reduced pressure to afford a yellow oil. Without further purification the ester was hydrolyzed using 10% sodium hydroxide (10 mL) in ethanol (25 mL) and allowing the reaction to stir overnight at room temperature. Ethanol was removed under reduced pressure at room temperature. The residual product was dissolved in water (100 mL) and washed with ethyl acetate (3×40 mL). The aqueous layer was acidified (pH 2) with concentrated hydrochloric acid and extracted with ethyl acetate (3×40 mL), dried over anhydrous MgSO$_4$, and evaporated to dryness to obtain a yellow solid. The product was recrystallized from a mixture of methylene chloride and hexane to yield a white powder, 1.07 g,66%. mp 183–187° C.

$^1$H NMR (CDCl$_3$): δ1.55 (d,3H,J=6.9 Hz), 2.17(s,6H), 3.52(s,2H), 4.65(q, 1H,J=6.7 Hz), 6.65(s,1H), 6.81 (d,2H, J=8.6 Hz), 6.98(s, 2H), 7.15(d,2H,J=8.6 Hz).

Anal. (C$_{19}$H$_{21}$NO$_4$); Calculated C 69.71, H 6.47, N 4.28; found C 69.58, H 6.49 and N 4.25

(−)-2-[4-[[(3,5-dimethylanilino)carbonyl]methyl]phenoxyl-propionic acid (18)

A solution of cinchonidine (4.50 g,15.3 mmol) in hot ethanol (70 mL) was added to a solution of (±)18 (5.00 g,15.3 mmol) in hot ethanol. The mixture was cooled to room temperature and a portion of the solvent was removed under reduced pressure. Crystals obtained were collected by filtration, 4.6 g, mp 198–200° C. The optical rotation was measured at 25° C.: [α]$_D$ −69.8°(c=0.2,methanol). The salt was recrystallized from ethanol to give pale yellow crystals, 2.86 g, mp 200–202° C. The optical rotation was measured at 25° C.: [α]$_D$ 71.0° (c=0.2,methanol). 2.7 g of the salt was dissolved in warm methanol (65 mL) and acidified to pH 2 with 1 N HCl The solution stirred for one hr and then the majority of the methanol was removed by rotavap. A white solid precipitated and was collected by filtration to obtain 1.3 g. mp 169–171° C. The optical rotation was measured at 21° C.: [α]$_D$ −25.6 (c=1, methanol).

Anal. (C$_{19}$H$_{21}$NO$_4$·0.5H$_2$O); Calculated C 67.84, H 6.59, N 4.16; found C 67.60, H 6.39 and N 4.41.

(+)-2-[4-[[(3,5-dimethylanilino)carbonyl]methyl]phenoxyl-propionic acid (18)

The enriched mother liquor, obtained after the first crystallization of (−) 18 was concentrated under reduced pressure. The residue was neutralized as described for (−) 18 to give a white solid, 2.3 g of optically pure (+) 30. mp 169–171° C. The optical rotation was measured at 21° C.: [α]$_D$ +25.1 (c=1, methanol).

Anal. (C$_{19}$H$_{21}$NO$_4$); Calculated C 69.71, H 6.47, N 4.28; found C 69.66, H 6.55 and N 4.32

Compound 19 was prepared using the same procedure as described above for (1 8).

2-[4-[[3,5-dimethylanilino)carbonyl]methyl]phenoxy-2-fluoroacetic acid (19)

Using ethyl bromofluoroacetate (2.9 g, 16 mmol), 8 (2.0 g, 7.8 mmol), and potassium carbonate (2.16 g, 15.6 mmol), compound 19 was prepared as described for 18, except the reaction went for two days. The brown oil obtained was purified by flash chromatography (eluent: hexane/ethyl acetate, 2:1) to afford a yellow oil. Ester hydrolysis afforded a yellow oil. The product was recrystallized from methylene chloride and hexane to yield a pale yellow powder, Yield 0.47 g, 18%. mp 123–1270C.

$^1$H NMR (CD$_3$OD): δ2.26 (s,6H), 3.64 (s,2H), 6.10 (d,1H,J=59.7 Hz), 6.75 (s,1H), 7.10 (d,2H,J=8.6 Hz), 7.16 (s,2H), 7.34 (d,2H,J=8.6 Hz).

Anal. (C$_{18}$H$_{18}$FNO$_4$); Calculated C 65.25, H 5.48, N 4.23; found C 65.32, H 5.49 and N 4.17

2-[4-[[(3,5-dimethylanilino)carbonyl]methyl]phenoxy]-butanoic acid (20)

Ethyl 2-bromobutyrte (3.9 g, 20 mmol) and 4-[[(3,5-dimethylanilino)carbonyl]methyl]phenol (2.5 g, 10 mmol) were reacted to yield the ethyl ester of 20, a yellow oil. Ester hydrolysis afforded a yellow solid, which upon recrystallization from methylene chloride and hexane gave a white solid, 2.86 g, 84%. mp 173–1750C.

$^1$H NMR (CDCl$_3$): δ1.08 (t,3H,J=7.5 Hz), 1.95 (m,2H), 2.25 (s,6H), 3.56 (s,2H), 4.61 (t,1H,J=7.0 Hz), 6.74 (s,1H), 6.86 (d,2H,J=8.6 Hz), 7.15 (s,2H), 7.25 (d,2H,J=8.6 Hz).

Anal. (C$_{20}$H$_{23}$NO$_4$); Calculated C 70.36, H 6.79, N 4.10; found C 70.09, H 6.76 and N 4.11

(−)-2-[4-[[(3,5-dimethylanilino)carbonyl]methyl]phenoxyl-butanoic acid (20)

Following the same procedure as described for (−) (18), cinchonidine (8.61 g, 29.3 mmol) in hot ethanol (175 mL) was added to a solution of (±) 20 (10.0 g, 29.3 mmol) in hot ethanol. The solution was allowed to cool to room temperature and a portion of the solvent was removed under reduced pressure. Crystals obtained were collected by filtration, 6.6 g, mp 204–205° C. The optical rotation was measured at 21° C. : $[\alpha]_D$ −73.3° (c=0.5, methanol). The salt was recrystallized from ethanol to give fluffy white crystals, 3.7 g, mp 206–207° C. The optical rotation was measured at 21° C. : $[\alpha]_D$ −74.2° (c=0.5, methanol). The acid was recovered from salt, as described previously for (−) 18, to obtain a white solid, 1.7 g. mp 150–151° C. The optical rotation was measured at 21° C.: $[\alpha]_D$ −28.4° (c=1.2, methanol).

Anal:($C_{20}H_{23}NO_4$); Calculated C 70.36, H 6.79, N 4.10; found C 70.17, H 6.86 and N 4.05

2-[4-[[(3,5-dimethylanilino)carbonyl]methyl] phenoxy]-2-methylbutanoic acid (21)

Compound 21 was prepared by reacting 4-[[(3,5-dimethylanilino)carbonyl]methyl]phenol (1.50 g, 5.88 mmol) and 2-butanone (4.23 g, 58.8 mmol) to yield a brown oil. The crude product was purified by flash chromatography (eluent: hexane/ethyl acetate 2:1) to obtain a yellow oil. Recrystallization from methylene chloride and hexane gave yellow crystals, 0.59 g, 28%. mp 131–133° C.

$^1$H NMR ($CD_3OD$): δ1.02 (t, 3H, J=7.3 Hz), 1.51 (s, 3H), 1.99 (m, 2H), 2.27 (s, 6H), 3.63 (s, 2H), 6.75 (s, 1H), 6.92 (d, 2H, J=7.0 Hz), 7.09 (s, 2H), 7.22 (d, 2H, J=7.1 Hz).

Anal: $C_{21}H_{25}NO_4$; Calculated C 70.96, H 7.09, N 3.94; found C 70.87, H 7.06 and N 3.89

2-{4-[(3,5-Dimethyl-phenylcarbamoyl)-hydroxy-methyl]-phenoxy}-2-methyl-propionic acid (12, KDD5-32)

To a stirring solution of 3,5-dimethylaniline (5.0 g, 41.3 mmol), mandelic acid (7.69 g, 41.3 mmol) and 1-hydroxybenzotriazole hydrate (6.14 g, 45.5 mmol) in dimethylformamide (100 mL) was added 1-(3-dimethylaminopropyl)-3-ethylcarbodiimide hydrochloride (8.73 g, 45.5 mmol) under nitrogen at room temperature. After stirring further for 16 hr, the reaction mixture was diluted with ethyl acetate (200 mL) and washed with 10% potassium hydrogen sulfate (2×50 mL), brine (50 mL), saturated sodium hydrogen carbonate (2×50 mL) and brine (50 mL). The organic phase was dried (MgSO4) and evaporated to give the product N-(3,5-Dimethyl-phenyl)-2-hydroxy-2-(4-hydroxy-phenyl) acetamide in 9.3 g yield.

The preparation of the ethyl ester was carried out using N-(3,5-Dimethyl-phenyl)-2-hydroxy-2-(4-hydroxy-phenyl) acetamide (4.0 g, 14.8 mmol), ethyl 2-bromoisobutyrate (19.2 g, 19.2 mmol), potassium carbonate (3.0 g, 22.1 mmol) in dimethylformamide (30 mL) to yield 2.9 g after column chromatography purification. Hydrolysis of the ester was carried out with (1.0 g, mmol) in ethanol (40 mL) and lithium hydroxide (1.05 g, 25 mmol) dissolved in water (20 mL). Purification by column chromatography gave 900 mg. m.p.

Anal: $C_{20}H_{23}NO_5 \cdot 0.25H_2O$ Calculated C 66.38; H 6.55; N 3.87; Found C 66.54; H 6.52; N3.81

2-{4-[(3,5-Dimethyl-phenylcarbamoyl)-ethoxy-methyl]-phenoxy}-2-methyl-propionic acid (13, KDD5-44)

To a stirring solution of 2-{4-[(3,5-Dimethyl-phenylcarbamoyl)-hydroxy-methyl]-phenoxy}-2-methyl-propionic acid ethyl ester (1.4 g, 3.6 mmol), in dry diethyl ether (10 mL) under nitrogen at 0° C. was added lead tribromide in methylene chloride (4.4 mL, 4.4 mmol) drop wise. The reaction mixture was further stirred at room temperature for 4 hr and concentrated. Water (100 mL) added and the product extracted with Ethyl acetate (3×50 mL), dried and evaporated to yield 1.0 g of 2-{4-[bromo-(3,5-dimethyl-phenylcarbamoyl)-ethoxy-methyl]-phenoxy}-2-methyl-propionic acid ethyl ester.

The ethyl ester (1.0 g, 2.2 mmol) in ethanol (30 mL) was added lithium hydroxide (214 mg, 9.0 mmol) dissolved in water (20 mL) and reaction mixture was stirred at room temperature overnight. The solvent was evaporated at room temperature and the residual product dissolved in water (100 mL) and extracted with ethyl acetate (2×50 mL). The aqueous phase was acidified with hydrochloride acid and extracted with ethyl acetate (4×40 mL) dried (MgSO4) and evaporated to give a pure product of 230 mg Anal: $C_{22}H_{27}NO_5$ Calculated C 68.55; H 7.06; N 3.63; Found C 68.52; H 7.07; N3.53

Enantiomeric Resolution by HPLC

The resolution of compounds 1, 2, 21 and purification of 20 was performed using a chiral semi-preparative HPLC column (CHIRACEL® OD, 1 cm×25 cm) packed with cellulose tris(3,5-dimethylphenyl carbamate) on a silica gel substrate. The samples were injected using a Waters 712 WISP automated injector system and detected with a Waters LAMBDA MAX (model 481) variable wavelength detector. All of the compounds were detected at 254 nm. The solvent delivery was controlled with a Waters Automated Gradient Controller (model 660). A Hewlett-Packard Integrator (HP 3393A) was used to integrate the peaks and to plot the chromatograms. The peak fractions were collected using a Spectrum CF-1 Fraction Collector. All solvents used for HPLC separation were purchased from Aldrich Chemical Co. as HPLC grade and filtered prior to use.

(+/−)-2-[4-[[(3,5-dimethylanilino)carbonyl]methyl] phenoxyl-2-methylbutanoic acid (21)

The compound was eluted with a mobile phase of heptane/ethanol with 1% TFA (89:11) at a flow rate of 2.0 mL/min. A stock solution (1 mg/mL) of the compound was prepared in ethanol/mobile phase (1:1). The injection sample volume was 250 pL. Under these conditions, the (−) isomer eluted at 20.7 min and the (+) isomer eluted at 22.9 min. The collected fractions were concentrated under reduced pressure at room temperature. (−) 21 was collected as a yellow solid, 0.11 g. mp 125–127° C. The optical rotation was measured at 20° C.: $[\alpha]_D$ −11.6° (c=0.3, methanol).

Anal: ($C_{21}H_{24}NO_4 \cdot 0.75H_2O \cdot 0.17TFA$); Calculated C,H, F,N.

$^1$H NMR ($CD_3OD$): δ0.99 (t,3H,J=7.4 Hz), 1.45 (s,3H), 1.96 (m,2H), 2.25 (s,6H), 3.58 (s,2H), 6.74 (s,1H), 6.87 (d,2H,J=8.6 Hz), 7.15 (d,2H), 7.24 (d,2H,J=8.5 Hz). (+) 10 was collected as a yellow solid 0.10 g. mp 127–129° C. The optical rotation was measured at 20° C.: $[\alpha]_D$ +11.0 (c=0.3, methanol).

Anal: ($C_{21}H_{24}NO_4 \cdot 0.5H_2O \cdot 0.25TFA$)

$^1$H NMR ($CD_3OD$): δ0.99 (t,3H,J=7.4 Hz), 1.45 (s,3H), 1.96 (m,2H), 2.25 (s,6H), 3.58 (s,2H), 6.74 (s,1H), 6.87 (d,2H,J=8.6 Hz), 7.15 (d,2H), 7.24 (d,2H,J=8.6 Hz).

(+)-2-[4-[[(3,5-dimethylanilino)carbonyl]methyl] phenoxy]-butanoic acid (20)

The mother liquor from the recrystallization of (−) 20-cinchonidine salt was concentrated under reduced pressure. The enriched (+) 20 isomer was obtained from the mother liquor by neutralizing the salt to obtain the free acid, as described previously for compound 18. The optical rotation showed that the isomer was approximately 80% enantiomeric excess, optical rotation was measured at $^{21°}$ C.: $[\alpha]_D$ +18:2° (c=1.2, methanol). A stock solution (1 mg/mL) of the racemic mixture (20) was prepared in ethanol/mobile phase (1:1). The injected sample volume was 250 μL. The compound was eluted with a mobile phase of heptane/ethanol. with 1% TFA (88:12) at a flow rate of 2.5 mL/min. Under these conditions, the (−) isomer eluted at 15.8 min and the (+) isomer eluted at 18.2 min retention times. The collected fractions were concentrated under reduced pressure at room temperature. (+) 20 was collected as a white solid, 0.14 g. mp 146–148° C. The optical rotation was measured at 21° C.: $[\alpha]_D$ +25.3° (c=0.5, methanol).

Anal: ($C_{20}H_{23}NO_4 \cdot 0.75H_2O$)

$^1$H NMR (CD$_3$OD): δ1.07 (t,3H,J=7.4 Hz), 1.95 (m,2H), 2.25 (s,6H), 3.57 (s,2H), 4.60 (t,1H,J=6.7 Hz), 6.74 (s,1H), 6.87 (d,2H,J=8.6 Hz), 7.15 (d,2H), 7.24 (d,2H,J=8.5 Hz).

(+/−)-3-[4-[[(3,5-dimethylanilino)carbonyl]methyl] phenoxy]-2-methyltetrahydro-3-furan carboxylic acid (2)

A stock solution (1 mg/mL) of the compound 2 was prepared in ethanol/mobile phase (1:1). The racemic compound after loading on HPLC was eluted with a mobile phase of heptane/ethanol with 1% TFA (85:15) at a flow rate of,2.75 mL/min. The injection sample volume was 1000 μL. Under these conditions, the (+) isomer eluted at 11.4 min and the (−) isomer eluted at 17.5 min. retention times. The collected fractions were concentrated under reduced pressure at room temperature. (+) 2, a pale yellow solid, was collected by filtration and washed with ether, 0.11 g. mp 164–167° C. The optical rotation was measured at 21° C.: $[\alpha]_D$ +67.5° (c=0.5, methanol).

Anal: ($C_{22}H_{25}NO_5 \cdot 0.75H_2O \cdot 0.125TFA$)

$^1$H NMR (CD$_3$OD): δ1.26 (d,3H,J=6.5 Hz), 2.25 (s,6H), 2.28 (m,1H), 2.85 (m,1H), 3.57 (s,2H), 3.85 (q,1H,J=7.3 Hz), 4.07 and 4.19 (m,1H), 6.74 (s,1H), 6.78 (d,2H,J=8.6 Hz), 7.15 (s,2H), 7.24 (d,2H,J=8.6 Hz).

(−) 2 was collected by filtration and washed with ether to give a beige solid, 0.10 g. mp 168–171° C. The optical rotation was measured at 21° C.: $[\alpha]_D$ −70.6° (c=0.3, methanol).

Anal: ($C_{22}H_{25}NO_5 \cdot 0.75H_2O \cdot 0.125TFA$)

$^1$H NMR (CD$_3$OD): δ1.26 (d,3H,J=6.5 Hz), 2.25 (s,6H, ArCH$_3$), 2.28 (m,1H), 2.87 (m,1H), 3.57 (s,2H), 3.85 (q,1H, J=8.1 Hz), 4.07 and 4.19 (m,1H), 6.74(s,1H), 6.78 (d,2H, J=8.6 Hz), 7.15 (s,2H), 7.24 (d,2H,J=8.4 Hz).

(+/−)-1-[4-[[(3,5-dimethylanilino)carbonyl]methyl] phenoxy]-2-methylcyclopentanecarboxylic acid (1)

A stock solution (1 mg/mL) of the compound was prepared in ethanol/mobile phase (1:1). The injection sample volume was 500 μL. The mixture was eluted with a mobile phase of heptane/ethanol with 1% TFA (90:10) at a flow rate of 2.0 mL/min. Under these conditions, the (+) isomer eluted at 18.9 min and the (−) isomer eluted at 26.2 min. retention times. The collected fractions were concentrated under reduced pressure at room temperature. (+) 1, a white solid, was collected by filtration and washed with ether, 0.11 g. mp 186–187° C. The optical rotation was measured at 21° C.: $[\alpha]_D$ +64.8° (c=0.5, methanol).

Anal: ($C_{23}H_{27}NO_4 \cdot 0.25H_2O$).

$^1$H NMR (CD$_3$OD): δ1.02 (d,3H,J=7.2 Hz), 1.43–2.48 (m,6H), 2.25 (s,6H), 2.51–2.57 (m,1H), 3.57 (s,2H), 6.74 (s,1H), 6.77 (d,2H,J=8.6 Hz), 7.15 (s,2H), 7.22 (d,2H,J=8.6 Hz).

The fractions for (−) 1 were collected and concentrated under reduced pressure. The white solid was collected by filtration and washed with ether, 0.11 g. mp 184–186° C. The optical rotation was measured at 21° C.: $[\alpha]_D$ −60.2° (c=0.5, methanol).

Anal: ($C_{23}H_{27}NO_4 \cdot 0.25H_2O$)

$^1$H NMR (CD$_3$OD): δ1.02 (d,3H,J=7.1 Hz), 1.42–2.47 (m,6H), 2.25 (s,6H), 2.49–2.57 (m,1H), 3.56 (s,2H), 6.74 (s,1H), 6.76 (d,2H,J=8.6 Hz), 7.15 (s,2H), 7.22 (d,2H,J=8.6 Hz).

Tables II and III show families of compounds having chiral centers and the $P_{50}$ value (partial pressure at which Hb is 50% saturated) for each compound.

TABLE II compounds based on structure A

STRUCTURE A

[Structure A: R1, R2-substituted phenyl-NH-C(=O)-CH(R3)-phenyl-O-C(R4)(R5)-COOH]

| No. | Name | Compound | Whole Blood Δp50 mm Hg |
|---|---|---|---|
| 1 | MKP14 | [3,5-dimethylphenyl-NH-C(=O)-CH2-phenyl-O-(2-methylcyclopentyl-1-COOH)] | 45.4 |
| 2 | MKP10 | [3,5-dimethylphenyl-NH-C(=O)-CH2-phenyl-O-(2-methyltetrahydrofuran-2-COOH)] | 15.2 |
| 3 | MKP1 | [3,5-dimethylphenyl-NH-C(=O)-CH2-phenyl-O-(3-methylcyclopentyl-1-COOH)] | 20.3 |
| 4 | MKP5 | [3,5-dimethylphenyl-NH-C(=O)-CH2-phenyl-O-(tetrahydropyran-4-COOH)] | 17.8 |
| 5 | MKP6 | [indan-5-yl-NH-C(=O)-CH2-phenyl-O-(3-methylcyclopentyl-1-COOH)] | 12.7 |
| 6 | MPK16 | [structure with H3C, CH2CH2CH3 groups] | 25.6 |

Compounds presented in Table III are the amino acid conjugates of RSR—based on structure B (21–36) and its corresponding cyclopentyl analog JP7 based on structure C (37–62).

TABLE III compounds based on structure B

STRUCTURE B (21–36)

STRUCTURE C (37–62)

| No. | Compound Name | $R_1$ | $R_2$ | Whole Blood $\Delta p50$ mm Hg |
|---|---|---|---|---|
| 21 | KDD4-24 | H | H | 17 |
| 22 | KDD4-28(D) | $CH_3$ | H | 17 |
| 23 | KDD5-128(L) | $CH_3$ | H | 22 |
| 24 | KDD4-29(L) | $CH(CH_3)_2$ | H | 22 |
| 25 | KDD4-71(D) | $CH(CH_3)_2$ | H | 20 |
| 26 | KDD4-62(DL) | $CH(CH_3)_2$ | H | 20 |
| 27 | KDD4-32(L) | $CH_2Ph$ | H | 10 |
| 28 | KDD5-134(D) | $CH_2Ph$ | H | 20 |
| 29 | KDD4-33(L) | $CH_2CH(CH_3)_2$ | H | 10 |
| 30 | KDD4-119(L) | $(CH_2)_2COOH$ | $CH_3$ | 26 |
| 31 | KDD4-122(L) | $CH_2COOH$ | $CH_3$ | 21 |
| 32 | KDD4-111(D) | $CH_2$tryptophan | H | 11 |
| 33 | KDD5-144(L) | $(Me)_2SMe$ | H | 16 |
| 34 | KDD5-145(D) | $(Me)_2SMe$ | H | 11 |
| 35 | KDD5-131(L) | $(CH_2)_3$ | H | 12 |
| 36 | KDD5-132(L) | $CH_2SCH_2Ph$ | H | 18 |
| 37 | AY-1(Gly) | H | H | 25 |
| 38 | AY-2(D-Ala) | $CH_3$ | H | 30 |
| 39 | AY-8(L-Ala) | $CH_3$ | H | 22 |
| 40 | AY-9(D-Leu) | $CH_2CH(CH_3)_2$ | H | 40 |
| 41 | AY-3(L-Leu) | $CH_2CH(CH_3)_2$ | H | 15 |
| 42 | AY-11(D-Val) | $CH(CH_3)_2$ | H | 27 |
| 43 | AY-4(L-Val) | $CH(CH_3)_2$ | H | 30 |
| 44 | AY-10(D-Phe) | $CH_2Ph$ | H | 38 |
| 45 | AY-5(L-Phe) | $CH_2Ph$ | H | 20 |
| 46 | AY-12(D-Try) | $CH_2$Indole | H | 20 |
| 47 | AY-6(L-Try) | $CH_2$Indole | H | 20 |
| 48 | AY-7(L-Glu) | $(CH_2)_2COOH$ | $CH_3$ | 22 |
| 49 | AY-19(D-Ser) | $CH_2OH$ | H | 16 |
| 50 | AY-14(L-Ser) | $CH_2OH$ | H | 5 |
| 51 | AY-15(D-Met) | $CH_2SCH_3$ | H | 27 |
| 52 | AY-13(L-Met) | $CH_2SCH_3$ | H | 21 |
| 53 | AY-16(L-He) | $CH(CH_3)C_2H_5$ | H | 13 |
| 54 | AY-17(L-Tyr) | $CH_2C_6H_4OH$ | H | 21 |
| 55 | AY-18(L-Asp) | $CH_2COOH$ | $CH_3$ | 27 |
| 56 | AY-20(L-Pro) | $(CH_2)_3$ | H | 17 |
| 57 | AY-21 (benzyl-L-cys) | $CH_2SCH_2Ph$ | H | 7 |
| 58 | AY-22(L-Thr) | $CH(OH)CH_3$ | H | 13 |
| 59 | AY-23 (benzyloxycarbonyl-L-Lys) | $(CH_2)_4NHCOOCH_2Ph$ | H | 0.4 |
| 60 | AY-24 benzyloxycarbonyl-D-Lys | $(CH_2)_4NHCOOCH_2Ph$ | H | 14 |
| 61 | AY25-D-Lys | $(CH_2)_4NH_2$ | H | −0.2 |
| 62 | AY26-L-Lys | $(CH_2)_4NH_2$ | H | −0.6 |

The synthesis of Table III compounds is described below:

The preparation of (2-(2-{4-[(3,5-Dimethyl-phenylcarbamoyl)-methyl]-phenoxy}-2-methyl-propionylamino)-acetic acid (21, KDD4-24) is a general reaction procedure. All of the RSR13-amino acid conjugate analogs (22–36) were prepared using a similar procedure.

To a stirring solution of RSR 13 (2.03 g, 6 mmol), glycine methyl ester hydrochloride (750 mg, 6 mmol) and 1-hydroxybenzotriazole hydrate (884 mg, 6.5 mmol) in dimethylformamide (30 mL) were added N-methylmorpholine (902 mg, 8.9 mmol) and 1-(3-dimethylaminopropyl)-3-ethylcarbodiimide hydrochloride (1.37 mg, 7.1 mmol) under nitrogen at room temperature. After stirring further for 16 hr, the reaction mixture was diluted with ethyl acetate (100 mL) and washed with 10% potassium hydrogen sulfate (2×50 mL), brine (50 mL), saturated sodium hydrogen carbonate (2×50 mL) and brine (50 mL). The organic phase was dried (MgSO4) and evaporated to give the pure corresponding ester, 2.57 g.

The ester 2.57 g in ethanol (60 mL) and aqueous lithium hydroxide (1.05 g, 25 mmol, 20 mL) was stirred at room temperature overnight. The solvent was evaporated at room temperature and the residual product dissolved in water (100 mL) and extracted with ethyl acetate (2×50 mL). The aqueous phase was acidified with hydrochloride acid and extracted with ethyl acetate (4×40 mL) dried (MgSO4) and evaporated to give a pure product of 2.18 g (92%).

Anal: $C_{22}H_{26}N_2O_5$ Calculated C 66.32; H 6.58; N 7.03; Found C 66.26; H 6.56; N 7.08

(2-(2-{4-[(3,5-Dimethyl-phenylcarbamoyl)-methyl]-phenoxy}-2-methyl-propionylamino)-propionic acid (D-, L-) (22 and 23, KDD4-28 & KDD5-128)

Using RSR13 acid (1.4 g, 4.1 mmol), appropriate (D or L) alanine methyl ester hydrochloride (575 mg, 4.1 mmol) and 1-hydroxybenzotriazole hydrate (610 mg, 4.5 mmol), N-methylmorpholine (622 mg, 6.2 mmol) and 1-(3-dimethylaminopropyl)-3-ethylcarbodiimide hydrochloride (946 mg, 4.9 mmol) in dimethylformamide (30 mL), the two isomers were prepared and isolated as described above for compound 21, in 1.67 g yield (98%).

Anal: $C_{23}H_{28}N_2O_5$ Calculated C 66.97; H 6.84; N 6.79; Found C 66.89; H 7.21; N 6.40

(2-(2-{4-[(3,5-Dimethyl-phenylcarbamoyl)-methyl]-phenoxy}-2-methyl-propionylamino)-3-methyl-butyric acid (24(L), 25(D) and 26 (DL), KDD4-29, 71 and 62)

Using RSR13 acid (1.5 g, 4.4 mmol), valine methyl ester hydrochloride (739 mg, 4.4 mmol) and 1-hydroxybenzotriazole hydrate (635 mg, 4.8 mmol), N-methylmorpholine (666 mg, 6.5 mmol) and 1-(3-dimethylaminopropyl)-3-ethylcarbodiimide hydrochloride (1.01 g, 5.3 mmol) in dimethylformamide (30 mL), the three isomers were prepared in 1.9 g yield (99%).

Anal: $C_{25}H_{32}N_2O_5$ Calculated C 68.16; H 7.32; N 6.36; Found C 67.94; H 7.42; N 6.28

(2-(2-{4-[(3,5-Dimethyl-phenylcarbamoyl)-methyl]-phenoxy}-2-methyl-propionylamino)-3-phenyl-propionic acid (27 (L) and 28 (D), (KDD4-32 & KDD5-134)

Using RSR13 acid (1.6 g, 4.7 mmol), phenylalanine methyl ester hydrochloride (1.08 mg, 4.7 mmol) and 1-hydroxybenzotriazole hydrate (697 mg, 5.2 mmol), N-methylmorpholine (711 mg, 7.0 mmol) and 1-(3- dimethylaminopropyl)-3-ethylcarbodiimide hydrochloride (1.08 g, 5.3 mmol) in dimethylformamide (40 mL), the two isomers were prepared in 2.2 g yield (96%).

Anal: $C_{29}H_{32}N_3O_5 \cdot 0.25H_2O$ Calculated C 70.64; H 6.64; N 5.68; Found C 70.75; H 6.75; N 5.49

(2-(2-{4-[(3,5-Dimethyl-phenylcarbamoyl)-methyl]-phenoxy}-2-methyl-propionylamino)-4-pentanoic acid (L) (29), (KDD4-33)

Using RSR13 acid (1.7 g, 5.0 mmol), leucine methyl ester hydrochloride (907 mg, 5.0 mmol) and 1-hydroxybenzotriazole hydrate (740 mg, 5.5 mmol), N-methylmorpholine (755 mg, 7.5 mmol) and 1-(3-dimethylaminopropyl)-3-ethylcarbodiimide hydrochloride (1.15 g, 6.0 mmol) in dimethylformamide (40 mL), the product was prepared in 2.2 g yield (97%).

Anal: $C_{26}H_{34}N_3O_5$ Calculated C 68.70; H 7.54; N 6.16; Found C 68.45; H 7.63; N 5.99

(2-(2-{4-[(3,5-Dimethyl-phenylcarbamoyl)-methyl]-phenoxy}-2-methyl-propionylamino)-pentanedioic acid 1-methyl ester (L) (30), (KDD4-119)

Using RSR13 acid (2.46 g, 7.2 mmol), glutamic acid β-t-butyl α-methyl ester hydrochloride (1.83 g, 7.2 mmol) and 1-hydroxybenzotriazole hydrate (1.07 g, 7.9 mmol), N-methylmorpholine (1.09 g, 10.8 mmol) and 1-(3-dimethylaminopropyl)-3-ethylcarbodiimide hydrochloride (1.65 g, 8.6 mmol) in dimethylformamide (30 mL), the diester was prepared in 3.8 g yield (98%) The mono methyl ester was prepared by hydrolysis of the tert-butoxycarbonyl ester (1.17 g, 2.2 mmol) in dry dichloromethane (30 mL) at 0 C. and in presence of trifluoroacetic acid (2 mL). The reaction mixture is stirred at room temperature overnight. The reaction will be worked up by diluting with dichloromethane (40 mL) and washing the organic layer with water (3×30 mL), followed by brine (30 mL). The dried (MgSO4) organic layer after evaporation and flash chromatography gave 900 mg (85%) of product.

Anal; $C_{26}H_{32}N_2O_7$ Calculated C 64.45; H 6.66; N 5.78; Found C 64.59; H 6.66; N 5.77

(2-(2-{4-[(3,5-Dimethyl-phenylcarbamoyl)-methyl]-phenoxy}-2-methyl-propionylamino)-succinic acid 1-methyl ester (L) (31), (KDD4-122)

Using RSR (2.71 g, 8.0 mmol), aspartic acid β-t-butyl α-methyl ester hydrochloride (1.91 g, 8.0 mmol) and 1-hydroxybenzotriazole hydrate (1.08 mg, 8.8 mmol), N-methylmorpholine (1.2 g, 11.9 mmol) and 1-(3-dimethylaminopropyl)-3-ethylcarbodiimide hydrochloride (1.83 g, 9.6 mmol) in dimethylformamide (30 mL), the diester was prepared in 4.2 g yield (98%) The mono methyl ester was prepared by hydrolysis of the tert-butoxycarbonyl ester (1.42 g, 2.7 mmol) in dry dichloromethane (40 mL) at 0 C. and in presence of trifluoroacetic acid (3 mL) as done in the case of KDD119. Flash chromatography purification gave 1.1 g (87%) of product.

Anal: $C_{25}H_{30}N_2O_7$ Calculated C 63.82; H 6.43; N 5.95; Found C 63.99; H 6.49; N 5.96

(2-(2-{4-[(3,5-Dimethyl-phenylcarbamoyl)-methyl]-phenoxy}-2-methyl-propionylamino)-3-(1H-indol-3-yl)-propionic acid (D) (32), (KDD4-111)

Using RSR13 acid (1.5 g, 4.4 mmol), tryptophan methyl ester hydrochloride (1.12 mg, 4.4 mmol) and 1-hydroxybenzotriazole hydrate (653 mg, 4.8 mmol), N-methylmorpholine (666 mg, 7.5 mmol) and 1-(3-dimethylaminopropyl)-3-ethylcarbodiimide hydrochloride (1.01 g, 6.0 mmol) in dimethylformamide (30 mL), the product was prepared in 2.3 g yield (96%)

Anal: $C_{31}H_{33}N_3O_5 \cdot 0.5H_2O$ Calculated C 69.39; H 6.39; N 7.83; Found C 69.46; H 6.48; N 7.62

2-(2-(4-((3,5-Dimethyl-phenylcarbamoyl)-methyl)-phenoxy)-2-methyl-propionylamino)-4-methylsulfanyl-butyric acid (L and D) (33, 34), (KDD5-144 and KDD5-145)

Using RSR13 Na salt (2.5 g, 6.9 mmol), and either D or L-methioine methyl ester hydrochloride (1.2 g, 6.9 mmol) and 1-hydroxybenzotriazole hydrate (1.02 g, 7.6 mmol) and 1-(3-dimethylaminopropyl)-3-ethylcarbodiimide hydrochloride (1.59 g, 8.3 mmol) in dimethylformamide (30 mL), afforded the product in 2.5 g yield (77%).

Anal $C_{25}H_{32}N_2O_5S$ Calculated C 63.54; H 6.82; N 5.93; S 6.78; Found C 63.56; H 6.79; N 5.88; S 6.73

(2-(2-{4-[(3,5-Dimethyl-phenylcarbamoyl)-methyl]-phenoxy}-2-methyl-propionyl)-pyrrolidine-2-carboxylic acid (L) (35), (KDD5-131)

Using RSR13 acid (3.08 g, 9.0 mmol), proline methyl ester hydrochloride (1.5 g, 9.0 mmol) and 1-hydroxybenzotriazole hydrate (1.34 g, 9.9 mmol), N-methylmorpholine (1.37 g, 13.6 mmol) and 1-(3-dimethylaminopropyl)-3-ethylcarbodiimide hydrochloride (2.08 g, 10.8 mmol) in dimethylformamide (40 mL), the product was prepared in 3.9 g yield (99%).

Anal: $C_{25}H_{30}N_2O_5$ Calculated C 68.47; H 6.90; N 6.39; Found C 68.32; H 7.31; N 5.99

3-Benzylsulfanyl-2-(2-(4-((3,5-Dimethyl-phenylcarbamoyl)-methyl)-phenoxy)-2-methyl-propionylamino)-propionic acid (L) (36), (KDD5-132)

Using RSR13 Na salt (6.93 g, 19.2 mmol), S-benzyl-L-cysteine methyl ester hydrochloride (5.0 g, 19.2 mmol) and 1-hydroxybenzotriazole hydrate (2.84 g, 21.1 mmol), N-methylmorpholine (2.9 g, 28.7 mmol) and 1-(3-dimethylaminopropyl)-3-ethylcarbodiimide hydrochloride (4.4 g, 22.9 mmol) in dimethylformamide (50 mL), afforded the product in 8.5 g yield (98%).

Anal $C_{30}H_{34}N_2O_5S$ Calculated C 67.39; H 6.41; N 5.24; S 6.00; Found C 67.27; H 6.49; N 5.21; S 5.91

The preparation of 1-[4-(((3,5-dimethylanilino)carbonyl)methyl)phenoxy]cyclopentane carbonyl glycine (37) (AY-1) is a general reaction procedure. All of the JP7 amino acid conjugate analogs (38–62) were prepared using a similar procedure.

To a stirring solution of 1-[4-(((3,5-dimethylanilino)carbonyl)methyl)phenoxy]cyclopentanecarboxylic acid (JP7 acid, 2.21 g, 6.0 mmol), glycine methyl ester hydrochloride (0.75 g, 6.0 mmol) and 1-hydroxybenzotriazole hydrate (0.88 g, 6.5 mmol) in dimethylformamide (30 ml) were added N-methylmorpholine (0.9 g, 8.9 mmol) and 1-(3-dimethylaminopropyl)-3-ethylcarbodiimide hydrochloride (1.36 mg, 7.1 mmol) under nitrogen at room temperature. After stirring for further 24 hrs, the reaction mixture was diluted with ethyl acetate (100 ml) and washed with water (40 ml). The ethyl acetate solution was further washed with 10% potassium hydrogen sulfate solution (2×50 ml), brine (50 ml), saturated sodium bicarbonate solution (2×50 ml) and brine (50 ml). The organic phase was dried over anhydrous magnesium sulfate, filtered, and evaporated under reduced pressure. The pure ester product was obtained by flash chromatography using hexane:ethyl acetate (1:1) as eluent; yield 2.32 g, 88.5%. mp 142–143° C. $^1$H NMR (CDCl$_3$) d 1.71–1.8 (m, 4H, cyclopentyl ring H), 2.04–2.14 (m, 2H, cyclopentyl ring H), 2.21 (s, 6H, aromatic CH$_3$), 2.25–2.34 (m, 2H, cyclopentyl ring H), 3.63 (s, 214, CH$_2$CO), 3.68 (s, 3H, COOCH$_3$), 4.04 (d,J=5.8, 2H, NHCH$_2$), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

The corresponding glycine methyl ester (1.0 g, 2.3 mmol), lithium hydroxide (0.11 g, 4.6 mmol) dissolved in water (10 ml) and ethanol (30 ml) was stirred at room temperature overnight. The solvent was evaporated on a rotavap at room temperature. The residual product was dissolved in water (100 ml) and extracted with ethyl acetate (2×50 ml). The aqueous phase was acidified with hydrochloric acid and extracted with ethyl acetate (4×40 ml). The organic phase was washed with brine (2×50 ml), dried over anhydrous magnesium sulfate, filtered, and evaporated to give a pure product; yield 0.8 g, 82.5%. mp 160–161° C. $^1$H NMR (CDCl$_3$) d 1.71–1.8 (m, 4H, cyclopentyl ring H), 2.04–2.14 (m, 2H, cyclopentyl ring H), 2.21 (s, 6H, aromatic CH$_3$), 2.25–2.34 (m, 2H, cyclopentyl ring H), 3.63 (s, 2H, CH$_2$CO), 4.04 (d, J=5.8, 2H, NHCH$_2$), 6.7 (s, 1H, aromatic H), 6.84 (d, J=8 Hz, 2H, aromatic H) 7.1 (s, 2H, aromatic H), 7.18 (d, J=8 Hz, 2H, aromatic H).

Anal: Calcd. for (C$_{24}$H$_{28}$N$_2$O$_5$): C, 67.91; H, 6.65; N, 6.60. Found: C, 67.75; H, 6.63;N, 6.51.

1-[4-(((3,5-dimethylanilino)carbonyl)methyl) phenoxy]cyclopentanecarbonyl-D-alanine (38)

Following previous procedure, JP7acid (2.21 g, 6.0 mmol) was reacted with D-alanine methyl-ester hydrochloride (0.84 g, 6.0 mmol), 1-hydroxybenzotriazole hydrate (0.88 g, 6.5 mmol), N-methylmorpholine (0.9 g, 8.9 mmol) and 1-(3-dimethylaminopropyl)-3-ethylcarbodiimide hydrochloride (1.36 mg, 7.1 mmol). The crude product obtained after workup was purified by flash chromatography using hexane:ethyl acetate (1:1); yield 2.35 g, 86.7%. mp 117–118° C. $^1$H NMR (CDCl$_3$) d 1.35 (d, J=7.2 Hz, 3H, CH$_3$), 1.68–1.76 (m, 4H, cyclopentyl ring H), 2.04–2.14 (m, 2H, cyclopentyl ring H), 2.2–2.4 (m, 8H, cyclopentyl ring H, & aromatic CH$_3$), 3.6 (s, 2H, CH$_2$CO), 3.65 (s, 3H, COOCH$_3$), 4.59 (m, 1H, CH), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

The title compound was synthesized similar to the previous reaction using the corresponding D-alanine methyl ester (1.04 g, 2.3 mmol). The final product was obtained upon recrystallization from ether and hexane; yield 0.9 g, 89.1%. mp 168–169° C. $^1$H NMR (CDCl$_3$) d 1.35 (d, J=7.2 Hz, 3H, CH$_3$), 1.68–1.76 (m, 4H, cyclopentyl ring H), 2.04–2.14 (m, 2H, cyclopentyl ring H), 2.2–2.4 (m, 8H, cyclopentyl ring H, & aromatic CH$_3$), 3.6 (s, 2H, CH$_2$CO), 4.59 (m, 1H, CH), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

Anal. Calcd. for (C$_{25}$H$_{30}$N$_2$O$_5$): C, 68.47; H, 6.90; N, 6.39. Found: C, 68.43; H, 6.85; N, 6.42.

1-[4-(((3,5-dimethylanilino)carbonyl)methyl) phenoxy] cyclopentanecarbonyl-L-alanine (39) was synthesized similar to the previous reaction using L-alanine methyl ester hydrochloride (0.84 g, 6 mmol). The crude product was purified by flash chromatography using hexane:ethyl acetate (1:1) as eluent; yield 2.0 g, 73.8%. mp 117–118° C. The title compound was synthesized similar to the previous reaction using the corresponding L-alanine methyl ester (1.04 g, 2.3 mmol). The final product was obtained upon recrystallization from ether and hexane; yield 0.92 g, 91.1%.mp 168–169° C.

Anal. Calcd. for (C$_{25}$H$_{30}$N$_2$O$_5$): C, 68.47; H, 6.90; N, 6.39. Found: C, 68.28; H, 7.01; N, 6.42.

1-[4-(((3,5-dimethylanilino)carbonyl)methyl) phenoxy] cyclopentanecarbonyl-D-leucine (40) was synthesized similar to the previous reaction using D-leucine methyl ester hydrochloride (1.1 g, 6.0 mmol). The crude ester was recrystallized using ether-hexane mixture; yield 2.22 g, 75%. mp 119–120° C. $^1$H NMR (CDCl$_3$) d 0.82 (2d, J=5.3 Hz, 6H, CH(CH$_3$)$_2$),1.42–1.6(m, 3H, CH$_2$CH), 1.74–1.8 (m, 4H, cyclopentyl ring H), 2.04–2.12 (m, 2H, cyclopentyl ring H), 2.21–2.34 (m, 8H, cyclopentyl ring H, & aromatic CH$_3$), 3.6 (s, 2H, CH$_2$CO), 3.65 (s, 3H, COOCH$_3$), 4.6 (m, 1H, NHCH), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

The title compound was synthesized similar to the previous reaction using the corresponding D-leucine methyl ester (1.14 g, 2.3 mmol); yield 0.94 g, 84.7%. mp 87–88° C. The optical rotation was measured at 25° C.: $[\alpha]_D$ +36.9 ° (c=0.1, methanol).$^1$H NMR (CDCl$_3$) d 0.82 (2d, J=5.3 Hz, 6H, CH(CH$_3$)$_2$),1.42–1.6(m, 3H, CH$_2$CH), 1.74–1.8 (m, 4H, cyclopentyl ring H), 2.04–2.12 (m, 2H, cyclopentyl ring H), 2.21–2.34 (m, 8H, cyclopentyl ring H, & aromatic CH$_3$), 3.6 (s, 2H, CH$_2$CO), 4.6 (m, 1H, NHCH), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

Anal. Calcd. for (C$_{28}$H$_{36}$N$_2$O$_5$): C, 69.98; H, 7.55; N, 5.83. Found: C, 69.93; H, 7.59; N, 5.78.

1-[4-(((3,5-dimethylanilino)carbonyl)methyl)phenoxy] cyclopentanecarbonyl-L-leucine (41) was synthesized similar to the previous reaction using L-leucine methyl ester hydrochloride (1.1 g, 6.0 mmol). The crude ester was purified by flash chromatography using hexane:ethyl acetate (2:1) as eluent; yield 2.31 g, 78%. mp 119–120° C.

The title compound was synthesized similar to the previous reaction using the corresponding L-leucine methyl ester (1.14 g, 2.3 mmol); yield 0.99 g, 89.2%.

mp 87–88° C. The optical rotation was measured at 25° C.: $[\alpha]_D$ +36.9° (c=0.1, methanol).

Anal. Calcd. for (C$_{28}$H$_{36}$N$_2$O$_5$): C, 69.98; H, 7.55; N, 5.83. Found: C, 69.82; H, 7.69; N, 5.72.

1-[4-(((3,5-dimethylanilino)carbonyl)methyl) phenoxy] cyclopentanecarbonyl-D-valine (42) was synthesized similar to the previous reaction using D-valine methyl ester hydrochloride (1.0 g, 6.0 mmol). The crude ester obtained after workup was purified by flash chromatography using hexane:ethyl acetate (2:1) as eluent. The final product was recrystallized using ether and hexane; yield 2.44 g, 85%. mp 104–105° C. $^1$H NMR (CDCl$_3$) d 0.73 (d, J=6.8 Hz, 3H, CHCH$_3$), 0.81 (d, J=6.8 Hz, 3H, CHCH3), 1.71–1.81 (m, 4H, cyclopentyl ring H), 2.04–2.18 (m, 3H, cyclopentyl ring H, & CH(CH$_3$)$_2$), 2.21–2.4 (m, 8H, cyclopentyl ring H, & aromatic CH$_3$), 3.6 (s, 2H, CH$_2$CO), 3.65 (s, 3H, COOCH$_5$), 4.5 (dd, J=5,10, 1H, NHCH), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

The title compound was synthesized similar to the previous reaction using the corresponding D-valine methyl ester (1.1 g, 2.3 mmol); yield 1.0 g, 93.5%. mp 81–82° C. $^1$H NMR (CDCl$_3$) d 0.73 (d, J=6.8, 3H, CHCH$_3$); 0.81 (d, J=6.8 Hz, 3H, CHCH$_3$), 1.71–1.81 (m, 4H, cyclopentyl ring H), 2.04–2.18 (m, 3H, cyclopentyl ring H, & CH(CH$_3$)$_2$), 2.21–2.4 (m, 8H, cyclopentyl ring H, & aromatic CH$_3$), 3.6 (s, 2H, CH$_2$CO), 4.5 (dd, J=5,10 Hz, 1H, NHCH), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

Anal. Calcd. for (C$_{27}$H$_{34}$N$_2$O$_5$.0.25H$_2$O): C, 68.84; H, 7.38; N, 5.95. Found: C, 68.96; H, 7.39; N, 5.83.

1-[4-(((3,5-dimethylanilino)carbonyl)methyl)phenoxy] cyclopentanecarbonyl-L-valine (43) was synthesized similar to the previous reaction using L-valine methyl ester hydrochloride (1.0 g, 6.0 mmol). The crude ester obtained after workup was purified by flash chromatography using hexane:ethyl acetate (2:1) as eluent; yield 2.64 g, 92%. mp 104–106° C. The title compound was synthesized similar to the previous reaction using the corresponding L-valine methyl ester (1.1 g, 2.3 mmol); yield 0.92 g, 86%. mp 81–82° C.

Anal. Calcd. for (C$_{27}$H$_{34}$N$_2$O$_5$.0.5H$_2$O): C, 68.19; H, 7.42; N, 5.89. Found: C, 68.03; H, 7.40; N, 5.80.

1-[4-(((3,5-dimethylanilino)carbonyl)methyl)phenoxy] cyclopentanecarbonyl-D-phenylalanine (44) was synthesized similar to the previous reaction using D-phenylalanine methyl ester hydrochloride (1.29 g, 6.0 mmol). The crude ester obtained after workup was recrystallized using ether-hexane mixture; yield 2.88 g, 91.1%. mp 106–108° C. $^1$H NMR (CDCl$_3$) d 1.7–1.81 (m, 4H, cyclopentyl ring H), 1.9–2.2 (m, 2H, cyclopentyl ring H), 2.21 (s, 6H, aromatic CH$_3$), 2.25–2.35(m, 2H, cyclopentyl ring H), 2.97 (dd, J=7.6,14.2 Hz, 1H, CH$_2$C$_6$H$_5$), 3.11 (dd, J=5.3,14.2 Hz, 1H, CH$_2$C$_6$H$_5$), 3.6 (s, 2H, CH$_2$CO), 3.65 (s, 3H, COOCH$_3$), 4.85 (m, 1H, NHCH), 6.65 (s, 1H, aromatic H), 6.71 (d, J=8 Hz, 2H, aromatic H), 6.95–7.18 (m, 9H, aromatic H).

The title compound was synthesized similar to the previous reaction using the corresponding D-phenylalanine methyl ester (1.21 g, 2.3 mmol); yield 1.1 g, 93.2%. mp 87–88° C. The optical rotation was measured at 25° C.: [α]$_D$ +8.2° (c=0.1, methanol). $^1$H NMR (CDCl$_3$) d 1.7–1.81 (m, 4H, cyclopentyl ring H), 1.9–2.2 (m, 2H, cyclopentyl ring H), 2.21 (s, 6H, aromatic CH$_3$), 2.25–2.35(m, 2H, cyclopentyl ring H), 2.97 (dd, J=7.6,14.2 Hz, 1H, CH$_2$C$_6$H$_5$), 3.11 (dd, J=5.3,14.2 Hz, 1H, CH$_2$C$_6$H$_5$), 3.6 (s, 2H, CH$_2$CO), 4.85 (m, 1H, NHCH), 6.65 (s, 1H, aromatic H), 6.71 (d, J=8 Hz, 2H, aromatic H), 6.95–7.18 (m, 9H, aromatic H).

Anal. Calcd. for (C$_{31}$H$_{34}$N$_2$O$_5$.0.25H$_2$O): C,71.72; H, 6.70; N, 5.40. Found: C,71.55; H, 6.82; N, 5.26.

1-[4-(((3,5-dimethylanilino)carbonyl)methyl)phenoxy] cyclopentanecarbonyl-L-phenylalanine (45) was synthesized similar to the previous reaction using L-phenylalanine methyl ester hydrochloride (1.29 g, 6.0 mmol). The crude ester obtained after workup was purified by flash chromatography using hexane:ethyl acetate (2:1) as eluent; yield 2.52 g, 79.7%. mp 106–107° C.

The title compound was synthesized similar to the previous reaction using the corresponding L-phenylalanine methyl ester (1.21 g, 2.3 mmol); yield 1.0 g, 84.7%. mp 87–88° C. Anal. Calcd. for (C$_{31}$H$_{34}$N$_2$O$_5$.0.25H$_2$O): C,71.72; H, 6.70; N, 5.40. Found: C,71.74; H, 6.73; N, 5.31.

1-[4-(((3,5-dimethylanilino)carbonyl)methyl)phenoxy] cyclopentanecarbonyl-D-tryptophan (46) was synthesized similar to the previous reaction using D-tryptophan methyl ester hydrochloride (1.53 g, 6.0 mmol). The crude ester obtained after workup was purified by flash chromatography using hexane:ethyl acetate (2:1) as eluent; yield 2.72 g, 80%. mp 83–84° C. $^1$H NMR (DMSO-d$_6$) d 1.6–1.8 (m, 4H, cyclopentyl ring H), 2.16–2.2 (m, 2H, cyclopentyl ring H ), 2.21 (s, 6H, aromatic CH$_3$), 2.25–2.4 (m, 2H, cyclopentyl ring H), 3.08 (dd, J=8.7,15 Hz, 1H, CH$_2$-indole), 3.3 (dd, J=4, 15 Hz, 1H, CH$_2$-indole), 3.5 (s, 2H, CH$_2$CO), 3.55 (s, 3H, COOCH$_3$), 4.76 (m, 1H, NHCH), 6.6 (s, 1H, aromatic H), 6.7 (d, J=8 Hz, 2H, aromatic H), 6.79 (s, 1H, indole NHCH), 6.9 (t, J=7.5 Hz, 1H, indoleH), 7.01 (t, J=7.5 Hz, 1H, indole H) 7.1 (s, 2H, aromatic H), 7.2 (d, J=8 Hz, 2H, aromatic H), 7.25 (d, J=7.5 Hz, 1H, indole H), 7.46 (d, J=7.5 Hz, 1H, indole H).

The title compound was synthesized similar to the previous reaction using the corresponding D-tryptophan methyl ester (1.3 g, 2.3 mmol); yield 1.2 g, 94.5%. mp 107–108° C. $^1$H NMR (DMSO-d$_6$) d 1.6–1.8 (m, 4H, cyclopentyl ring H), 2.16–2.2 (m, 2H, cyclopentyl ring H), 2.21 (s, 6H, aromatic CH$_3$), 2.25–2.4 (m, 2H, cyclopentyl ring H), 3.08 (dd, J=8.7,15 Hz, 1H, CH$_2$-indole), 3.3 (dd, J=4, 15 Hz, 1H, CH$_2$-indole), 3.5 (s, 2H, CH$_2$CO), 4.76 (m, 1H, NHCH), 6.6 (s, 1H, aromatic H), 6.7 (d, J=8 Hz, 2H, aromatic H), 6.79 (s, 1H, indole NHCH), 6.9 (t, J=7.5 Hz, 1H, indoleH), 7.01 (t, J=7.5 Hz, 1H, indole H) 7.1 (s, 2H, aromatic H), 7.2 (d, J=8 Hz, 2H, aromatic H), 7.25 (d, J=7.5 Hz, 1H, indole H), 7.46 (d, J=7.5 Hz, 1H, indole H).

Anal. Calcd. for (C$_{33}$H$_{35}$N$_3$O$_5$): C,71.59; H, 6.37; N, 7.59. Found: C, 71.42; H, 6.51; N, 7.38.

1-[4-(((3,5-dimethylanilino)carbonyl)methyl)phenoxy] cyclopentanecarbonyl-L-tryptophan (47) was synthesized similar to the previous reaction using L-tryptophan methyl ester hydrochloride (1.53 g, 6.0 mmol). The crude ester obtained after workup was purified by flash chromatography using hexane:ethyl acetate (2:1) as eluent; yield 2.95 g, 86.8%. mp 83–84° C.

The title compound was synthesized similar to the previous reaction using the corresponding D-tryptophan methyl ester (1.3 g, 2.3 mmol); yield 1.2 g, 94.5%. mp 107–108° C.

Anal. Calcd. for (C$_{33}$H$_{35}$N$_3$O$_5$.0.75H$_2$O): C, 69.88; H, 6.49; N, 7.41. Found: C, 70.02; H, 6.36; N, 7.33.

1-[4-(((3,5-dimethylanilino)carbonyl)methyl)phenoxy] cyclopentanecarbonyl-D-methionine (51) was synthesized similar to the previous reaction using D-methionine methyl ester hydrochloride (1.2 g, 6.0 mmol). The crude ester obtained after workup was purified by flash chromatography using hexane:ethyl acetate (2:1) as eluent; yield 2.8 g, 96%. mp 54–55° C. $^1$H NMR (CDCl$_3$) d 1.76–1.81 (m, 4H, cyclopentyl ring H), 1.91–2.0 (m, 4H, CHCH$_2$CH$_2$, & cyclopentyl ring H), 2.1–2.4 (m, 13H, cyclopentyl ring H, aromatic CH$_3$, & CH$_2$SCH$_3$), 3.6 (s, 2H, CH$_2$CO), 3.7 (s, 3H, COOCH$_3$), 4.66 (m, 1H, NHCH), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

The title compound was synthesized similar to the previous reaction using the corresponding D-methionine methyl ester (1.64 g, 2.3 mmol); yield 1.28 g, 80%. mp 62–63° C. $^1$H NMR (CDCl$_3$) d 1.76–1.81 (m, 4H, cyclopentyl ring H), 1.91–2.0 (m, 4H, CHCH$_2$CH$_2$, & cyclopentyl ring H), 2.1–2.4 (m, 13H, cyclopentyl ring H, aromatic CH$_3$, & CH$_2$SCH$_3$), 3.6 (s, 2H, CH$_2$CO), 4.66 (m, 1H, NHCH), 6.7 (s, 1H, aromatic H), 6.84 (d, J=8 Hz, 2H, aromatic H), 7.1 (s, 2H, aromatic H), 7.18 (d, J=8 Hz, 2H, aromatic H).

Anal. Calcd. for (C$_{27}$H$_{34}$N$_2$O$_5$S): C, 65.04; H, 6.87; N, 5.62; S, 6.43. Found: C, 64.76; H, 7.04; N, 5.47; S, 6.24.

1-[4-(((3,5-dimethylanilino)carbonyl)methyl)phenoxy] cyclopentanecarbonyl-L-methionine (52) was synthesized similar to the previous reaction using L-methionine methyl ester hydrochloride (1.2 g, 6.0 mmol). The crude ester obtained after workup was purified by flash chromatography using hexane:ethyl acetate (2:1) as eluent; yield 2.74 g, 93.8%. mp 54–56° C.

The title compound was synthesized similar to the previous reaction using the corresponding L-methionine methyl ester (1.64 g, 2.3 mmol); yield 1.33 g, 83.1%. mp 62–63° C.

Anal. Calcd. for ($C_{27}H_{34}N_2O_5S$): C, 65.04; H, 6.87; N, 5.62; S, 6.43. Found: C, 65.13; H, 7.04; N, 5.38; S, 6.16.

1-[4-(((3,5-dimethylanilino)carbonyl)methyl)phenoxy]cyclopentanecarbonyl-D-serine (49) was synthesized similar to the previous reaction using D-serine methyl ester hydrochloride (0.93 g, 6.0 mmol). The crude ester obtained after workup was purified by flash chromatography using ethyl acetate as eluent; yield 2.52 g, 94.7%. mp 58–59° C. $^1$H NMR (DMSO-$d_6$) d 1.64–1.81 (m, 4H, cyclopentyl ring H), 2.16–2.2 (m, 2H, cyclopentyl ring H), 2.21 (s, 6H, aromatic $CH_3$), 2.25–2.4 (m, 2H, cyclopentyl ring H), 3.5 (s, 2H, $CH_2CO$), 3.55 (s, 3H, $COOCH_3$), 3.6 (dd, J=3, 11 Hz, 1H, $CH_2OH$), 3.72 (dd, J=4, 11 Hz, 1H, $CH_2OH$), 4.24 (m, 1H, NHCH), 6.7 (s, 1H, aromatic H), 6.84 (d, J=8 Hz, 2H, aromatic H), 7.1 (s, 2H, aromatic H), 7.2 (d, J=8 Hz, 2H, aromatic H).

The title compound was synthesized similar to the previous reaction using the corresponding D-serine methyl ester (1.08 g, 2.3 mmol); yield 0.94 g, 89.5%. mp 73–75° C. $^1$H NMR (DMSO-$d_6$) d 1.64–1.81 (m, 4H, cyclopentyl ring H), 2.16–2.2 (m, 2H, cyclopentyl ring H), 2.21 (s, 6H, aromatic $CH_3$), 2.25–2.4 (m, 2H, cyclopentyl ring H), 3.5 (s, 2H, $CH_2CO$), 3.6 (dd, J=3, 11 Hz, 1H, $CH_2OH$), 3.72 (dd, J=4, 11 Hz, 1H, $CH_2OH$), 4.24 (m, 1H, NHCH), 6.7 (s, 1H, aromatic H), 6.84 (d, J=8 Hz, 2H, aromatic H), 7.1 (s, 2H, aromatic H), 7.2 (d, J=8 Hz, 2H, aromatic H).

Anal. Calcd. for ($C_{25}H_{30}N_2O_6.0.5H_2O$): C, 64.78; H, 6.74; N, 6.04. Found: C, 64.77; H, 6.91; N, 5.69.

1-[4-(((3,5-dimethylanilino)carbonyl)methyl)phenoxy]cyclopentanecarbonyl-L-serine (50) was synthesized similar to the previous reaction using L-serine methyl ester hydrochloride (0.93 g, 6.0 mmol). The crude ester obtained after workup was purified by flash chromatography using ethyl acetate as eluent; yield 2.51 g, 94.4%. mp 58–59° C.

The title compound was synthesized similar to the previous reaction using the corresponding L-serine methyl ester (1.08 g, 2.3 mmol); yield 0.93 g, 88.6%. mp 73–74° C.

Anal. Calcd. for ($C_{25}H_{30}N_2O_6.0.25H_2O$): C, 65.42; H, 6.10; N, 6.04. Found: C, 65.53; H, 6.88; N, 5.74.

$N^\alpha$-1-[4-(((3,5dimethylanilino)carbonyl)methyl)phenoxy]cyclopentanecarbonyl-$N^e$-benzyloxycarbonyl-D-lysine (60) was synthesized similar to the previous reaction using $N^e$-benzyloxycarbonyl-D-lysine methyl ester hydrochloride (1.99 g, 6.0 mmol). The crude ester was purified by flash chromatography using hexane:ethyl acetate (1:1) as eluent; yield 3.6 g, 93.5%. mp 53–55° C. $^1$H NMR (CDCl$_3$) d 1.1–1.35 (m, 4H, CHCH$_2$CH$_2$), 1.76–1.85 (m, 4H, cyclopentyl ring H), 2.02–2.14 (m, 2H, cyclopentyl ring H), 2.21 (s, 6H, aromatic CH$_3$), 2.25–2.4 (m, 2H, cyclopentyl ring H), 2.95–3.05 (m, 4H, CH$_2$CH$_2$NH), 3.6 (s, 2H, CH$_2$CO), 3.65 (s, 3H, COOCH$_3$), 4.55 (m, 1H, NHCH), 5.15 (s, 2H, CH$_2$O), 6.7 (s, 1H, aromatic H), 6.84 (d, J=8 Hz, 2H, aromatic H), 7.1–7.35 (m, 9H, aromatic H).

The title compound was synthesized similar to the previous reaction using the corresponding $N^e$-benzyloxycarbonyl-D-lysine methyl ester (1.48 g, 2.3 mmol); yield 1.34 g, 92.4%. mp 61–62° C. $^1$H NMR (CDCl$_3$) d 1.1–1.35 (m, 4H, CHCH$_2$CH$_2$), 1.76–1.85 (m, 4H, cyclopentyl ring H), 2.02–2.14 (m, 2H, cyclopentyl ring H), 2.21 (s, 6H, aromatic CH$_3$), 2.25–2.4 (m, 2H, cyclopen-tyl ring H), 2.95–3.05 (m, 4H, CH$_2$CH$_2$NH), 3.6 (s, 2H, CH$_2$CO), 4.55 (m, 1H, NHCH), 5.15 (s, 2H, CH$_2$O), 6.7 (s, 1H, aromatic H), 6.84 (d, J=8 Hz, 2H, aromatic H), 7.1–7.35 (m, 9H, aromatic H).

Anal. Calcd. for ($C_{36}H_{43}N_3O_7$): C, 68.66; H, 6.88; N, 6.67. Found: C, 68.92; H, 7.03; N, 6.63.

$N^e$-1-[4-(((3,5dimethylanilino)carbonyl)methyl)phenoxy]cyclopentanecarbonyl-$N^e$-benzyloxycarbonyl-L-lysine (59) was synthesized similar to the previous reaction using $N^e$-benzyloxycarbonyl-L-lysine methyl ester hydrochloride (0.93 g, 6.0 mmol). The crude ester obtained after workup was purified by flash chromatography using hexane:ethyl acetate (1:1) as eluent; yield 3.28 g, 85.2%. mp 53–55° C.

The title compound was synthesized similar to the previous reaction using the corresponding $N^e$-benzyloxycarbonyl-L-lysine methyl ester (1.48 g, 2.3 mmol); yield 1.3 g, 87.9%. mp 61–62° C.

Anal. Calcd. for ($C_{36}H_{43}N_3O_7.0.5H_2O$): C, 67.69; H, 6.94; N, 6.58. Found: C, 67.73; H, 6.96; N, 6.36.

1-[4-(((3,5-dimethylanilino)carbonyl)methyl)phenoxy]cyclopentanecarbonyl-L-isoleucine (53) was synthesized similar to the previous reaction using L-isoleucine methyl ester hydrochloride (1.1 g, 6.0 mmol). The crude ester obtained after workup was purified by flash chromatography using hexane:ethyl acetate (2:1) as eluent; yield 2.31 g, 78%. mp 127–128° C. $^1$H NMR (CDCl$_3$) d 0.82 (t, J=7.3 Hz, 3H, CH$_2$CH$_3$), 0.9 (d, J=6.8 Hz, 3H, CHCH$_3$), 0.98–1.4 (m, 3H, CHCH$_2$), 1.69–1.81 (m, 4H, cyclopentyl ring H), 2.02–2.18 (m, 2H, cyclopentyl ring H), 2.21 (s, 6H, aromatic CH$_3$), 2.25–2.45 (m, 2H, cyclopentyl ring H), 3.6 (s, 2H, CH$_2$CO), 3.65 (s, 3H, COOCH$_3$), 4.48 (dd, J=6, 8.4 Hz, 1H, NHCH), 6.7 (s, 1H, aromatic H), 6.84 (d, J=8 Hz, 2H, aromatic H), 7.1 (s, 2H, aromatic H), 7.2 (d, J=8 Hz, 2H, aromatic H).

The title compound was synthesized similar to the previous reaction using the corresponding L-isoleucine methyl ester (1.14 g, 2.3 mmol); yield 0.97 g, 87.4%. mp 72–73° C. $^1$H NMR (CDCl$_3$) d 0.82 (t, J=7.3 Hz, 3H, CH$_2$CH$_3$), 0.9 (d, J=6.8 Hz, 3H, CHCH$_3$), 0.98–1.4 (m, 3H, CHCH$_2$), 1.69–1.81 (m, 4H, cyclopentyl ring H), 2.02–2.18 (m, 2H, cyclopentyl ring H), 2.21 (s, 6H, aromatic CH$_3$), 2.25–2.45 (m, 2H, cyclopentyl ring H), 3.6 (s, 2H, CH$_2$CO), 4.48 (dd, J=6, 8.4 Hz, 1H, NHCH), 6.7 (s, 1H, aromatic H), 6.84 (d, J=8 Hz, 2H, aromatic H), 7.1 (s, 2H, aromatic H), 7.2 (d, J=8 Hz, 2H, aromatic H). Anal. Calcd. for ($C_{28}H_{36}N_2O_5.0.5H_2O$): C, 68.69; H, 7.62; N, 5.72. Found: C, 68.49; H, 7.61; N, 5.54.

1-[4-(((3,5-dimethylanilino)carbonyl)methyl)phenoxy]cyclopentanecarbonyl-L-tyrosine (54) was synthesized similar to the previous reaction using L-tyrosine methyl ester hydrochloride (1.39 g, 6.0 mmol). The crude ester obtained after workup was purified by flash chromatography using hexane:ethyl acetate (2:1) as eluent; yield 2.84 g, 87.1%. mp 74–75° C. $^1$H NMR (CDCl$_3$) d 1.7–1.81 (m, 4H, cyclopentyl ring H), 2.03–2.17 (m, 2H, cyclopentyl ring H), 2.21 (s, 6H, aromatic CH$_3$), 2.25–2.34 (m, 2H, cyclopentyl ring H), 2.75 (dd, J=9.5, 13.5 Hz, 1H, CH$_2$C$_5$H$_6$O), 3.15 (dd, J=4.3, 13.5 Hz, 1H, CH$_2$C$_5$H$_6$O), 3.6 (s, 2H, CH$_2$CO), 3.65 (s, 3H, COOCH$_3$), 4.6 (m, 1H, NHCH), 6.4 (s, 1H, aromatic H), 6.45 (d, J=8 Hz, 2H, aromatic H), 6.65 (d, J=8.5 Hz, 2H, aromatic H), 6.7 (d, J=8.5 Hz, 2H, aromatic H), 6.8 (s, 2H, aromatic H), 7.0 (d, J=8 Hz, 2H, aromatic H).

The title compound was synthesized similar to the previous reaction using the corresponding L-tyrosine methyl ester (1.25 g, 2.3 mmol); yield 1.1 g, 90.2%. mp 97–98° C. $^1$H NMR (CDCl$_3$) d 1.7–1.81 (m, 4H, cyclopentyl ring H), 2.03–2.17 (m, 2H, cyclopentyl ring H), 2.21 (s, 6H, aromatic $CH_3$), 2.25–2.34 (m, 2H, cyclopentyl ring H), 2.75 (dd, J=9.5, 13.5 Hz, 1H, $CH_2C_5H_6O$), 3.15 (dd, J=4.3, 13.5 Hz, 1H, $CH_2C_5H_6O$), 3.6 (s, 2H, $CH_2CO$), 4.6 (m, 1H, NHCH), 6.4 (s, 1H, aromatic H), 6.45 (d, J=8 Hz, 2H, aromatic H), 6.65 (d, J=8.5 Hz, 2H, aromatic H), 6.7 (d, J=8.5 Hz, 2H, aromatic H), 6.8(s, 2H, aromatic H), 7.0 (d, J=8 Hz, 2H, aromatic H).

Anal. Calcd. for ($C_{31}H_{34}N_2O_6 \cdot 0.25H_2O$): C, 69.58; H, 6.50; N,5.23. Found: C, 69.68; H, 6.73; N, 5.05.

1-[4-(((3,5-dimethylanilino)carbonyl)methyl)phenoxy]cyclopentanecarbonyl-L-proline (56) was synthesized similar to the previous reaction using L-proline methyl ester hydrochloride (0.99 g, 6.0 mmol). The crude ester obtained after workup was purified by flash chromatography using hexane:ethyl acetate (2:1) as eluent; yield 2.3 g, 80.1%. mp 71–72° C. $^1$H NMR ($CDCl_3$) d 1.69–1.81 (m, 4H, cyclopentyl ring H), 1.89–2.43 (m, 14H, cyclopentyl ring H, aromatic $CH_3$, & proline $CH_2$), 3.6 (s, 2H, $CH_2CO$), 3.64–3.7 (m, 5H, $COOCH_3$, & $NHCH_2$), 4.5 (dd, J=4.3, 7.3, 1H, NHCH), 6.4 (s, 1H, aromatic H), 6.45 (d, J=8 Hz, 2H, aromatic H), 6.8(s, 2H, aromatic H), 7.0 (d, J=8 Hz, 2H, aromatic H).

The title compound was synthesized similar to the previous reaction using the corresponding L-proline methyl ester (1.1 g, 2.3 mmol); yield 0.94 g, 93.1%. mp 90–91° C. $^1$H NMR ($CDCl_3$) d 1.69–1.81 (m, 4H, cyclopentyl ring H), 1.89–2.43 (m, 14H, cyclopentyl ring H, aromatic $CH_3$, & proline $CH_2$), 3.6 (s, 2H, $CH_2CO$), 3.65 (m, 2H, $NHCH_2$), 4.5 (dd, J=4.3, 7.3, 1H, NHCH), 6.4 (s, 1H, aromatic H), 6.45 (d, J=8 Hz, 2H, aromatic H), 6.8(s, 2H, aromatic H), 7.0 (d, J=8 Hz, 2H, aromatic H).

Anal. Calcd. for ($C_{27}H_{33}N_2O_5 \cdot 0.25H_2O$): C, 68.99; H, 7.18; N, 5.96. Found: C, 69.00; H, 6.98; N, 5.78.

1-[4-(((3,5-dimethylanilino)carbonyl)methyl)phenoxy]cyclopentanecarbonyl S-benzyl-L-cysteine (57) was synthesized similar to the previous reaction using S-benzyl-L-cysteine methyl ester hydrochloride (1.57 g, 6.0 mmol). The crude ester was separated as oil and purified by flash chromatography using hexane:ethyl acetate (1:2) as eluent; yield 3.12 g, 90.7%. $^1$H NMR ($CDCl_3$) d 1.78–1.81 (m, 4H, cyclopentyl ring H), 2.08–2.18 (m, 2H, cyclopentyl ring H), 2.21–2.4 (m, 8H, cyclopentyl ring H, & aromatic $CH_3$), 2.74 (dd, J=7, 14 Hz, 1H, $CH_2S$), 2.84 (dd, J=5, 14 Hz, 1H, $CH_2S$), 3.6 (s, 2H, $CH_2CO$), 3.65 (s, 3H, $COOCH_3$), 3.85(s, 2H, $SCH_2C_6H_5$), 4.72 (m, 1H, NHCH), 6.7 (s, 1H, aromatic H), 6.84 (d, J=8 Hz, 2H, aromatic H), 6.97(s, 2H, aromatic H), 7.03 (d, J=8 Hz, 2H, aromatic H), 7.14–7.27 (m, 5H, aromaticH).

The title compound was synthesized similar to the previous reaction using the corresponding S-benzyl-L-cysteine methyl ester (1.32 g, 2.3 mmol); yield 1.23 g, 95.3%. mp 130–132° C. $^1$H NMR ($CDCl_3$) d 1.78–1.81 (m, 4H, cyclopentyl ring H), 2.08–2.18 (m, 2H, cyclopentyl ring H), 2.21–2.4 (m, 8H, cyclopentyl ring H, & aromatic $CH_3$), 2.74 (dd, J=7, 14 Hz, 1H, $CH_2S$), 2.84 (dd, J=5, 14 Hz, 1H, $CH_2S$), 3.6 (s, 2H, $CH_2CO$), 3.85(s, 2H, $SCH_2C_6H_5$), 4.72 (m, 1H, NHCH), 6.7 (s, 1H, aromatic H), 6.84 (d, J=8 Hz, 2H, aromatic H), 6.97(s, 2H, aromatic H), 7.03 (d, J=8 Hz, 2H, aromatic H), 7.14–7.27 (m, 5H, aromaticH). Anal. Calcd. for ($C_{32}H_{36}N_2O_5S$): C, 68.55; H, 6.47; N, 5.00; S, 5.72. Found: C, 68.32; H, 6.55; N, 5.00; S, 5.57.

1-[4-(((3,5-dimethylanilino)carbonyl)methyl)phenoxy]cyclopentanecarbonyl-L-threonine (58) was synthesized similar to the previous reaction using L-threonine methyl ester hydrochloride (1.02 g, 6.0 mmol). The crude ester obtained after workup was purified by flash chromatography using hexane:ethyl acetate (2:1) as eluent; yield 2.7 g, 93.4%. mp 64–66° C. $^1$H NMR ($CDCl_3$) d 1.02(d, J=6.5 Hz, 3H, $CH_3$), 1.76–1.81 (m, 4H, cyclopentyl ring H), 2.07–2.18 (m, 2H, cyclopentyl ring H), 2.21–2.4 (m, 8H, cyclopentyl ring H, & aromatic $CH_3$), 3.6 (s, 2H, $CH_2CO$), 3.65 (s, 3H, $COOCH_3$), 4.32 (m, 1H, CHOH), 4.47 (dd, J=2.4, 8.5 Hz, 1H, NHCH), 6.4 (s, 1H, aromatic H), 6.45 (d, J=8 Hz, 2H, aromatic H), 6.8(s, 2H, aromatic H), 7.0 (d, J=8 Hz, 2H, aromatic H).

The title compound was synthesized similar to the previous reaction using the corresponding L-threonine methyl ester (1.11 g, 2.3 mmol); yield 0.84 g, 83.2%. mp 82–83° C. $^1$H NMR ($CDCl_3$) d 1.02(d, J=6.5 Hz, 3H, $CH_3$), 1.76–1.81 (m, 4H, cyclopentyl ring H), 2.07–2.18 (m, 2H, cyclopentyl ring H), 2.21–2.4 (m, 8H, cyclopentyl ring H, & aromatic $CH_3$), 3.6 (s, 2H, $CH_2CO$), 4.32 (m, 1H, CHOH), 4.47 (dd, J=2.4, 8.5 Hz, 1H, NHCH), 6.4 (s, 1H, aromatic H), 6.45 (d, J=8 Hz, 2H, aromatic H), 6.8(s, 2H, aromatic H), 7.0 (d, J=8 Hz, 2H, aromatic H).

Anal. Calcd. for ($C_{26}H_{32}N_2O_6$): C, 66.65; H, 6.88; N, 5.98. Found: C, 66.51; H, 6.96; N, 5.87.

1-[4-(((3,5-dimethylanilino)carbonyl)methyl)phenoxy]cyclopentanecarbonyl-L-aspartate (55). Following a similar procedure, JP7 (2.21 g, 6.0 mmol) was reacted with L-aspartate-γ-t-butyl ester hydrochloride (1.44 g, 6.0 mmol), 1-hydroxybenzotriazole hydrate (0.88 g, 6.5 mmol), N-methylmorpholine (0.9 g, 8.9 mmol) and 1-(3-dimethylaminopropyl)-3-ethylcarbodiimide hydrochloride (1.36 mg, 7.1 mmol). The crude product was purified by flash chromatography using hexane:ethyl acetate (2:1) as eluent; yield 2.31 g, 70%. mp 47–48° C. $^1$H NMR ($CDCl_3$) d 1.4 (s, 9H, $C(CH_3)_3$), 1.75–1.81 (m, 4H, cyclopentyl ring H), 2.02–2.19 (m, 2H, cyclopentyl ring H), 2.21 (s, 6H, aromatic $CH_3$), 2.25–2.34 (m, 2H, cyclopentyl ring H), 2.82 (dd, J=4.5, 7.8 Hz, 2H, $CH_2COOH$), 3.61 (s, 2H, $CH_2CO$), 3.68 (s, 3H, $COOCH_3$), 4.6 (m, 1H, NHCH), 6.7 (s, 1H, aromatic H), 6.84 (d, J=8 Hz, 2H, aromatic H), 6.97(s, 2H, aromatic H), 7.03 (d, J=8 Hz, 2H, aromatic H).

Trifluoroacetic acid (2 ml) was added to the corresponding tertiarybutoxycarbonyl ester (1.27 g, 2.3 mmol) in dry dichloromethane (30 ml) at 0° C. The mixture was stirred at room temperature overnight. After completion of the reaction, the mixture was diluted with dichloromethane (40 ml), washed with water (3×30 ml) and brine (30 ml). The organic phase was dried over anhydrous magnesium sulfate, filtered, and evaporated under reduced pressure. The pure product was obtained by flash chromatography using ethyl acetate as eluent; yield 1.0 g, 87.7%. mp 63–65 ° C. $^1$H NMR ($CDCl_3$) d 1.75–1.81 (m, 4H, cyclopentyl ring H), 2.02–2.19 (m, 2H, cyclopentyl ring H), 2.21 (s, 6H, aromatic $CH_3$), 2.25–2.34 (m, 2H, cyclopentyl ring H), 2.82 (dd, J=4.5, 7.8 Hz, 2H, $CH_2COOH$), 3.61 (s, 2H, $CH_2CO$), 3.68 (s, 3H, $COOCH_3$), 4.6 (m, 1H, NHCH), 6.7 (s, 1H, aromatic H), 6.84 (d, J=8 Hz, 2H, aromatic H), 6.97(s, 2H, aromatic H), 7.03 (d, J=8 Hz, 2H, aromatic H).

Anal. Calcd. for ($C_{27}H_{32}N_2O_7$): C, 65.31; H, 6.50; N, 5.64. Found: C, 65.29; H, 6.42; N, 5.80.

1-[4-(((3,5-dimethylanilino)carbonyl)methyl)phenoxy]cyclopentanecarbonyl-L-glutamate (48) was synthesized similar to the previous reaction using L-glutamate-γ-t-butyl ester hydrochloride (1.52 g, 6.0 mmol). The crude ester obtained after workup was purified by flash chromatography using hexane:ethyl acetate (2:1) as eluent; yield 2.38 g, 70%. mp 50–51° C. $^1$H NMR ($CDCl_3$) d 1.41 (s, 9H, $C(CH_3)_3$), 1.7–1.9 (m, 6H, cyclopentyl ring H, & $CH_2COOC(CH_3)_3$), 2.02–2.21 (m, 8H, cyclopentyl ring H, & aromatic CH$_3$), 2.25–2.5 (m, 4H, cyclopentyl ring H, & NHCHCH$_2$), 3.6 (s, 2H, CH$_2$CO), 3.7 (s, 3H, COOCH$_3$), 4.55 (m, 1H, NHCH), 6.7 (s, 1H, aromatic H), 6.84 (d, J=8 Hz, 2H, aromatic H), 6.97(s, 2H, aromatic H), 7.03 (d, J=8 Hz, 2H, aromatic H).

The title compound was synthesized similar to the previous reaction using the corresponding L-glutamate-γ-t-butyl ester (1.27 g, 2.3 mmol). The crude product was purified by flash chromatography using ethyl acetate as eluent; yield 0.94 g, 80.3%. mp 60–61° C. $^1$H NMR (CDCl$_3$) d 1.7–1.9 (m, 6H, cyclopentyl ring H, & CH$_2$COOC(CH$_3$)$_3$), 2.02–2.21 (m, 8H, cyclopentyl ring H, & aromatic CH$_3$), 2.25–2.5 (m, 4H, cyclopentyl ring H, & NHCHCH$_2$), 3.6 (s, 2H, CH$_2$CO), 3.7 (s, 3H, COOCH$_3$), 4.55 (m, 1H, NHCH), 6.7 (s, 1H, aromatic H), 6.84 (d, J=8 Hz, 2H, aromatic H), 6.97(s, 2H, aromatic H), 7.03 (d, J=8 Hz, 2H, aromatic H).

Anal. Calcd. for (C$_{28}$H$_{34}$N$_2$O$_7$): C, 65.87; H, 6.71; N, 5.49. Found: C, 65.72; H, 6.84; N, 5.38.

1-[4-(((3,5-dimethylanilino)carbonyl)methyl)phenoxy]cyclopentanecarbonyl-D-lysine (61). To the corresponding N$^e$-benzyloxycarbonyl-D-lysine (18) (0.5 g, 0.79 mmol) in ethanol (10 ml), was added 10% palladium on carbon. The mixture was hydrogenated in the Parr-Shaker until absorption of the hydrogen gas was stopped. The catalyst was filtered, washed with ethanol (2×25 ml) and the combined filtrate was evaporated under reduced pressure. The pure product was obtained upon recrystallization from chloroform; yield 0.33 g, 84.6%. mp 124–125 ° C. $^1$H NMR (CDCl$_3$) d 1.1–1.35 (m, 4H, CHCH$_2$CH$_2$), 1.76–1.85 (m, 4H, cyclopentyl ring H), 2.02–2.14 (m, 2H, cyclopentyl ring H), 2.21 (s, 6H, aromatic CH$_3$), 2.25–2.4 (m, 2H, cyclopentyl ring H), 2.95–3.05 (m, 4H, CH$_2$CH$_2$NH), 3.6 (s, 2H, CH$_2$CO), 4.55 (m, 1H, NHCH), 6.7 (s, 1H, aromatic H), 6.84 (d, J=8 Hz, 2H, aromatic H), 6.97(s, 2H, aromatic H), 7.03 (d, J=8 Hz, 2H, aromatic H).

Anal. Calcd. for (C$_{28}$H$_{37}$N$_3$O$_5$.0.5 C$_2$H$_5$OH): C, 67.16; H, 7.77; N, 8.10. Found: C, 67.05; H, 7.95; N, 7.84.

1-[4-(((3,5-dimethylanilino)carbonyl)methyl)phenoxy]cyclopentanecarbonyl-L-lysine (62) was synthesized similar to the previous reaction using the corresponding N$^e$-benzyloxycarbonyl-L-lysine(19) (0.5 g, 0.79 mmol). The final product was obtained upon recrystallization from chloroform; yield 0.35 g, 89.7%. mp 124–125° C. $^1$H NMR (CDCl$_3$) d 1.1–1.35(m, 4H, CHCH$_2$CH$_2$), 1.76–1.85 (m, 4H, cyclopentyl ring H), 2.02–2.14 (m, 2H, cyclopentyl ring H), 2.21 (s, 6H, aromatic CH$_3$), 2.25–2.4 (m, 2H, cyclopentyl ring H), 2.95–3.05 (m, 4H, CH$_2$CH$_2$NH), 3.6 (s, 2H, CH$_2$CO), 4.55 (m, 1H, NHCH), 6.7 (s, 1H, aromatic H), 6.84 (d, J=8 Hz, 2H, aromatic H), 6.97(s, 2H, aromatic H), 7.03 (d, J=8 Hz, 2H, aromatic H).

Anal. Calcd. for (C$_{28}$H$_{37}$N$_3$O$_5$.0.5 C$_2$H$_5$OH): C, 67.16; H, 7.77; N, 8.10. Found: C, 66.85; H, 7.86; N, 7.74.

Biological Evaluation

Structure-allosteric activity relationships were determined from the synthetic chiral effectors comparing the shift in the oxygen binding curve of Hb solutions using a Hemox-Analyzer. In vitro biological activity testing in the presence of plasma proteins was also performed. on selected enantiomers and racemates (multi-point tonometry and blood gas analysis) to screen for candidates with potential clinical use. SAR studies compared the degree in shift in P$_{50}$ values, i.e., the partial pressure of molecular oxygen necessary to half-saturate hemoglobin. An effector that decreases Hb oxygen affinity increases the P$_{50}$ value relative to the control. Thus, the activity or potency of each analog could be expressed by the ratio P$_{50}$ (effector)/P$_{50}$(control). Tables and II and III summarize the P50 values obtained using human whole blood, while Tables IV and V summarize the P$_{50}$ and the Hill coefficient values (n$_{50}$) at half-saturation obtained using Hemox-analyzer. The slope of the log of the oxygen binding curves is known-as the Hill coefficient. The Hill coefficient measures the degree of cooperativity in binding for an allosteric protein, the normal range for human blood is 2.7–3.2. Table VI presents the results from the whole blood studies given as a ΔP$_{50}$ and Hill coefficient (n$_{50}$) values for the enantiomers and racemates.

All of the derivatives prepared were able to influence the P$_{50}$ value (partial pressure at which Hb is 50% saturated) to varying degrees when analyzed in Hb solutions. Structure-activity relationships were formulated for table II compounds from the Hb solution studies. The 2-methylcyclopentyl substituted analog was the most potent allosteric effector. Methyl substitution on the cyclopentyl ring was better tolerated in the 2-position than the 3-position. Increasing the size of the alkyl ring to a 6-membered ring reduced activity. Yet, single alkyl groups longer than the methyl enhanced activity, butyl>propyl>ethyl>methyl. Furthermore, it was observed that increasing the length of one of the gem dimethyls to an ethyl also reduced activity. In general, though, oxygen substitutions in the cycloalkyl ring reduced allosteric activity.

Structure-activity relationships also showed that there was a difference in activity between enantiomers. These results are shown in tables V and VI. The stereocenter had an effect on activity. The activities of the resolved enantiomers with alkyl substitutions (aliphatic open chain analogs) showed that the (+)(R)isomer was more potent than the (−)(S)isomer. Among the cycloalkyl enantiomers, the (−)isomer was more potent than the (+)isomer. Yet, the (−)isomer has the (1R,2R) configuration and the (+)-isomer has the (1S,2S) configuration.

X-ray crystallography studies of select enantiomers complexed with Hb showed that the less potent enantiomer formed water-mediated salt bridges with the Arg residue. The direct salt bridge between the effector and Hb tends to weaken a critical T-state salt bridge that Arg 141α2 makes with Asp 126α1. It appeared that the orientation of the alkyl or cycloalkyl group within the small hydrophobic pocket determined the nature of the salt bridge. A direct salt bridge is a stronger interaction than a water-mediated one. This suggests that the less potent isomer has a higher affinity for the binding site than the more potent isomer which would allow for competition between enantiomers for the binding site. This observation could explain why the activity of the racemates for some compounds were not an average of the results for the enantiomeric pair.

Overall, this study showed that chirality has an effect on allosteric activity and binding orientation. The (−)isomer of the 2-methylcyclopentyl derivative was shown to be more active than RSR13 in the Hb solution studies and comparable in activity when tested in vitro using whole blood.

Crystallization from ethanol of (±)2-[4-[[(3,5-dimethylanilino)carbonyl]methyl]phenoxy]-propionic acid cinchonidine salt, the monomethyl analog of RSR13, gave (−)2-[4-[[(3,5-dimethylanilino)carbonyl]methyl]phenoxy]-propionic acid. The optically pure antipode, (+)2-[4-[[(3,5-dimethylanilino)carbonyl]methyl]phenoxy]-propionic acid, was recovered from the mother liquor by crystallization. The same method was used to obtain the monoethyl RSR13 analog (−)2-[4-[[(3,5-dimethylanilino)carbonyl]methyl]

phenoxy]-butanoic acid. Enriched (+)2-[4-[[(3,5-dimethylanilino)carbonyl]methyl]phenoxy]-butanoic acid was obtained from the mother liquor by crystallization. Enantiomers of JP7 analogs 1-[4-[[(3,5-dimethylanilino)carbonyl]methyl]phenoxy]-2-methylcyclopentyl and 3-[4-[[(3,5-dimethylanilino)carbonyl]methyl]phenoxy]-2-methyltetrahydrofuran and the methylethyl RSR13 analog 2-[4-[[(3,5-dimethylanilino)carbonyl]methyl]phenoxy]-2-methylbutanoic acid were separated and isolated using a CHIRACEL OD semi-preparative HPLC column. The column was also used in the purification of enriched (+)2-[4-[[(3,5-dimethylanilino)carbonyl]methyl]phenoxy]-butanoic acid.

Analysis of the alkyl substituted analogs, 2-[4-[[(3,5-dimethylanilino)carbonyl]methyl]phenoxy]-2-methylbutanoic acid, 2-[4-[[(3,5-dimethylanilino)carbonyl]methyl]phenoxy]-propionic acid and 2-[4-[[(3,5-dimethylanilino)carbonyl]methyl]phenoxy]-butanoic acid, on the CHIRACEL OD column revealed that the (−)isomer eluted first the (+)isomer second. Cycloalkyl racemates 1-[4-[[(3,5-dimethylanilino)carbonyl]methyl]phenoxy]-2-methylcyclopentane carboxylic acid and 3-[4-[[(3,5-dimethylanilino)carbonyl]methyl]phenoxyl-2-methyltetrahyro-3-furan carboxylic acid showed the opposite pattern with the (+) isomer eluting first and the (−) isomer second. Furthermore, HPLC chromatograms showed that the racemates 1-[4-[[(3,5-dimethylanilino)carbonyl]methyl]phenoxy]-2-methylcyclopentane carboxylic acid and 3-[4-[[(3,5-dimethylanilino)carbonyl]methyl]phenoxy]-2-methyltetrahyro-3-furan carboxylic acid were composed of only two of the four possible stereo-isomers. Sharp melting points, optical rotation measurements, and proton NMR of the purified enantiomers confirmed the presence of only one set of diastereomers.

The absolute configurations of the enantiomers were not established. Configurational studies on 2-phenoxy propionic acids have shown that isomers with (−)rotation have the (S) configuration, and (+)isomers have the (R) configuration. However, it is not possible by direct comparison of the optical rotation of the structurally similar phenoxy acids to unequivocally establish the stereochemical assignments of the alkyl substituted RSR 13 analogs as (+)(R) and (−)(S).

The appearance of only one. set of diastereomers for the methylcyclopentyl or methylcyclotetrahydrofuran derivatives 1-[4-[[(3,5-dimethylanilino)carbonyl]methyl]phenoxy]-2-methylcyclopentane carboxylic acid and 3-[4-[[(3,5-dimethylanilino)carbonyl]methyl]phenoxy]-2-methyltetrahyro-3-furan carboxylic acid was rationalized. Attack by the phenoxide ion on the least sterically hindered dichloroepoxide intermediates of 1-[4-[[(3,5-dimethylanilino)carbonyl]methyl]phenoxy]-2-methylcyclopentane carboxylic acid and 3-[4-[[(3,5-dimethylanilino)carbonyl]methyl]phenoxy]-2-methyltetrahyro-3-furan carboxylic acid with the configuration 1R,2S and 1S,2R suggest that one set of diasteromers would be favored. Crystallographic studies to be published elsewhere confirm the stereochemistry of (+/−) 1-[4-[[(3,5-dimethylanilino)carbonyl]methyl]phenoxy]-2-methylcyclopentane carboxylic acid diasteromeric pair suggested by the mechanism.

TABLE IV

Results of hemoglobin solution studies for synthesized analogs[a]

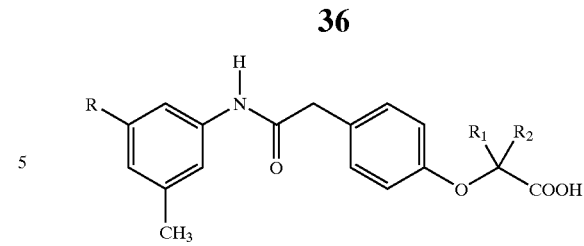

R = CH₃ (9–16,30–34)
R = Cl (27–29, 35, 36)

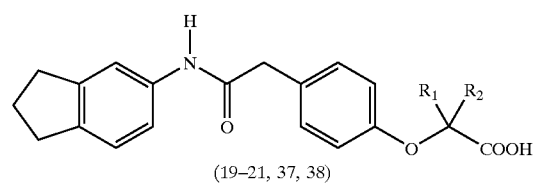

(19–21, 37, 38)

| No. | R₁ | R₂ | $P_{50}e^b$ | $P_{50}e/P_{50}c^c$ | $n_{50}{}^d$ |
|---|---|---|---|---|---|
| RSR13 | CH₃ | CH₃ | 23 | 4.7 | 2.3 |
| KDD86 | Cl | CH₃ | 21 | 4.4 | 2.4 |
| RSR46 | CH₃ | CH₃ | 15 | 3 | 2.6 |
| JP7 | cyclopentyl | | 26 | 5.1 | 2.4 |
| 1 | 2-methylcyclopentyl | | 22 | 4.3 | 2.3 |
| 2 | 2-methyltetrahydrofuran | | 7.6 | 1.5 | 2.4 |
| 3 | 3-methylcyclopentyl | | 13 | 2.6 | 2.5 |
| 4 | 4-tetrahydropyran | | 7.6 | 1.5 | 2.4 |
| 5 | 3-methylcyclopentyl | | 13 | 2.5 | 2.6 |
| 6 | CH₃ | CH₂CH₂CH₃ | 12 | 2.3 | 2.7 |
| 7 | 2-methylcyclopentyl | | 14 | 2.8 | 2.6 |
| 8 | 2-methylcyclopentyl | | 22 | 4.4 | 2.4 |
| 9 | 2-methylcyclopentyl | | 14 | 2.8 | 2.4 |
| 10 | CH₃ | CH₂OCH₃ | 8.4 | 1.7 | 2.4 |
| 11 | 3-methylcyclohexyl | | 10 | 2.1 | 2.5 |
| 18 | CH₃ | H | 9.3 | 1.9 | 2.6 |
| 19 | F | H | 5.9 | 1.2 | 2.5 |
| 20 | CH₂CH₃ | H | 13 | 2.6 | 2.7 |
| 21 | CH₃ | CH₂CH₃ | 13 | 2.7 | 2.4 |

[a]All studies were carried out at 50–60 mM heme concentration in the present of 0.5 mM effector concentration. All solutions were prepared in 100 mM bis-Tris buffer, pH 7.2. See Experimental Section for more details.
[b]$P_{50}e$ is the oxygen pressure in mmHg at which Hb is 50% saturated with oxygen in the present of the effector.
[c]Ratio of $P_{50}e$ to $P_{50}c$ ($P_{50}$ control value with no effector present, 5.0 mmHg).
[d]The Hill coefficient at 50% satureation ($n_{50}$) is calculated from the Hill equation by linear-regression analysis of data points between 40 and 60% oxygen saturation ($n_{50}$ control value with no effector present, 2.7).

TABLE V

Results of hemoglobin solution studies for resolved enantiomers[a]

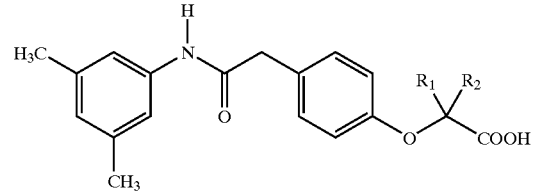

| No. | R₁ | R₂ | $P_{50}e^b$ | $P_{50}e/P_{50}c^c$ | $n_{50}{}^d$ |
|---|---|---|---|---|---|
| (+)21 | CH₃ | CH₂CH₃ | 17.4 | 3.5 | 2.4 |
| (−)21 | CH₃ | CH₂CH₃ | 10.5 | 2.1 | 2.3 |
| (+)(1S,2S,)1 | 2-methylcyclopentyl | | 19.9 | 4 | 2.6 |
| (−)(1R,2R)1 | 2-methylcyclopentyl | | 30.7 | 6.1 | 2.4 |
| (+)2 | 2-methyltetrahydrofuran | | 7.7 | 1.5 | 2.8 |
| (−)2 | 2-methyltetrahydrofuran | | 9.3 | 1.9 | 2.6 |
| (+)18 | CH₃ | H | 9.8 | 2 | 2.6 |
| (−)18 | CH₃ | H | 6.6 | 1.3 | 2.5 |
| (+)20 | CH₂CH₃ | H | 18 | 3.6 | 2.7 |
| (−)20 | CH₂CH₃ | H | 9.8 | 2 | 2.8 |

TABLE V-continued

Results of hemoglobin solution studies for resolved enantiomers[a]

[Structure: H3C-substituted phenyl with CH3, connected via NH-C(=O)-CH2 to phenyl-O-C(R1)(R2)-COOH]

| No. | R1 | R2 | $P_{50}e$[b] | $P_{50}e/P_{50}c$[c] | $n_{50}$[d] |
|-----|----|----|----|----|----|

[a]All studies were carried out at 50–60 mM heme concentration in the presence of 0.5 mM effector concentration. All solutions were prepared in 100 mM bis-Tris buffer, pH 7.2. See experimental section for more details.
[b]$P_{50}e$ is the oxygen pressure in mmHg at which Hb is 50% saturated with oxygen in the present of the effector.
[c]Ratio of $P_{50}e$ to $P_{50}c$ ($P_{50}$ control value with no effector present, 5.0 mmHg).
[d]The Hill coefficient at 50% satureation ($n_{50}$) is calculated from the Hill equation by linear-regression analysis of data points between 40 and 60% oxygen saturation ($n_{50}$ control value with no effector present, 2.7).

TABLE VI

Results of In Vitro Whole Blood Studies[a]

[Structure: H3C-substituted phenyl with CH3, connected via NH-C(=O)-CH2 to phenyl-O-C(R1)(R2)-COOH]

| No. | R1 | R2 | $P_{50}c$[b] | $P_{50}e$[c] | $\Delta P_{50} \pm S.D.$[d] | $n_{50}e \pm S.D.$[e] |
|-----|----|----|----|----|----|----|
| (±)1 | 2-methyl-cyclopentyl | | 26.5 | 66 | | |
| | | | | 67.2 | 40.1 ± 0.9 | |
| (+)(1S,2S)1 | 2-methyl-cyclopentyl | | 25.7 | 49.7 | | |
| | | | | 46.8 | | |
| | | | | 42.4 | 20.6 ± 3.6 | |
| (−)(1R,2R)1 | 2-methyl-cyclopentyl | | 27.9 | 78.5 | | |
| | | | | 72.5 | 47.6 ± 4.2 | |
| (±)18 | CH3 | H | 27.2 | 47.2 | | |
| | | | | 43.5 | 18.2 ± 2.6 | |
| (+)18 | CH3 | H | 27.3 | 47.4 | | |
| | | | | 48.7 | 20.7 ± 0.7 | |
| (−)18 | CH3 | H | 27.8 | 39.7 | | |
| | | | | 40.5 | 12.3 ± 0.6 | |
| RSR13 | CH3 | CH3 | 29.8 | 76.5 | | |
| | | | | 73.4 | 45.2 ± 2.2 | |
| JP7 | cyclopentyl | | 28.9 | 74.7 | | |
| | | | | 67.7 | 42.3 ± 4.9 | |

[a]All studies were carried out at 2.5 mM Hb concentration in the presence of 5.0 mM effectro concentration. All solutions were prepared in DMSO. See Experimental Section for more details.
[b]$P_{50}$ control value in mmHg, (average $P_{50}c$ value = 27.6 ± 1.3, n = 8)
[c]$P_{50}$ value in the presence of the effector in mmHg.
[d]$\Delta P_{50}$ = ($P_{50}$ effector − $P_{50}$ control) in mmHg.
[e]The Hill coefficient at 50% saturation ($n_{50}$) in the presence of effector (average $n_{50}$ control value = 2.7 ± 0.1, n = 8).

Structure Activity Relationships

The new analogs differ in their substitution at the gem-dimethyl position α to the carboxylate group. All of the synthesized derivatives from this study increased $P_{50}$ exhibiting a wide range of allosteric effector activity (Table IV). In general, similarly substituted compounds from the 3,5-dimethylphenyl and the 3,5-chloromethylphenyl series appeared to be equal in potency. Corresponding compounds with the indanyl group substitution were less active. The majority of the compounds showed good cooperativity in Hb solutions, $n_{50}$=2.3–2.7 (table IV).

Removal of one of the methyl groups from the gem dimethyl position, significantly reduced activity. Substitution of fluoro group for methyl resulted in further decreased activity. The length of the monoalkyl group enhances activity. The activity of compounds with monoalkyl substitution tended to increase with the size of the group (butyl≧propyl≧ethyl≧methyl). The effect seemed to plateau going from the propyl to the butyl group with only a slight increase in the $P_{50}$. Replacement of one of the methyl groups with an ethyl group decreased activity by one-half, and increasing the length of the chain further reduced $P_{50}$ (table IV). The position of the methyl substitution on the cyclopentyl ring appears to be important, 2-methyl being>3-methyl . The 2-methylcyclopentyl compound 1-[4-[[(3,5-dimethylanilino)carbonyl]methyl]phenoxy]-2-methylcyclopentane carboxylic acid was nearly twice as active as the 3-methyl derivative 1-[4-[[(3,5-dimethylanilino)carbonyl]methyl]phenoxy]-3-methylcyclopentane carboxylic acid. A slight loss in activity was observed when the size of the cycloalkyl ring was increased to a six-membered ring. Oxygen substitutions to alkyl chains and cycloalkyl groups reduced activity. This observation was most apparent with compound 3-[4-[[(3,5-dimethylanilino)carbonyl]methyl]phenoxy]-2-methyltetrahydro-3-furan carboxylic acid. Compounds 1-[4-[[(3,5-dimethylanilino)carbonyl]methyl]phenoxy]-2-methylcyclopentane carboxylic acid and 3-[4-[[(3,5-dimethylanilino)carbonyl]methyl]phenoxy]-2-methyltetrahydro-3-furan carboxylic acid are structurally similar except for an ether oxygen substitution in the cyclopentyl ring, yet 1-[4-[[(3,5-dimethylanilino)carbonyl]methyl]phenoxy]-2-methylcyclopentane carboxylic acid was nearly three time more potent than 3-[4-[[(3,5-dimethylanilino)carbonyl]methyl]phenoxy]-2-methyltetrahydro-3-furan carboxylic acid. Compound 1-[4-[[(3,5-dimethylanilino)carbonyl]methyl]phenoxy]-2-methylcyclopentane carboxylic acid was the most potent compound from the study exhibiting activity comparable to RSR13 and JP7.

In general, the result of the enantiomers showed that the stereocenter does have an effect on allosteric activity (table V). A small difference in the $P_{50}$ values was observed between the enantiomers of 2-[4-[[(3,5-dimethylanilino)carbonyl]methyl]phenoxy]-propionic acid; the (+)2-[4-[[(3,5-dimethylanilino)carbonyl]methyl]phenoxy]-propionic acid was slightly more active than the (−)2-[4-[[(3,5-dimethylanilino)carbonyl]methyl]phenoxy]-propionic acid. The same trend was observed for the isomers of 20. The (+) isomer was nearly twice as active as its mirror image, (−)isomer. (+)20 was more potent than (+)2-[4-[[(3,5-dimethylanilino)carbonyl]methyl]phenoxy]-propionic acid, which further indicated that the longer alkyl group enhances activity. A similar difference in activity between the enantiomers of 21 was also observed, (+)21>(−)21. The difference in activity between the enantiomers of compound 2 did not appear to be as significant. The most interesting observation among the enantiomers involved compound 1. The results showed that (−) (1R,2R)1 was more potent than the (+)(1S,2S)1 isomer, and furthermore, (−)1 was more potent in Hb solutions than both RSR13 and JP7 with a $P_{50}$ of 30.7 mm Hg (Table V). The activity observed for some of the racemates was not an average of the $P_{50}$ value for the enantiomeric pair.

The racemates and the enantiomers of compounds 1-[4-[[(3,5-dimethylanilino)carbonyl]methyl]phenoxy]-2- methylcyclopentane carboxylic acid and 2-[4-[[(3,5-dimethylanilino)carbonyl]methyl]phenoxy]-propionic acid were also analyzed in vitro using human whole blood. Results from the whole blood study revealed the same general trend in activity as observed in Hb solutions. The compounds lowered the $n_{50}$ which means to a small extent all of the compounds reduce the cooperativity of Hb. Generally, compounds with a high $P_{50}$ value cause the $n_{50}$ to decrease. (+)2-[4-[[(3,5-dimethylanilino)carbonyl]methyl]phenoxy]-propionic acid was more potent that (−)2-[4-[[(3,5-dimethylanilino)carbonyl]methyl]phenoxy]-propionic acid. In addition, (−)1-[4-[[(3,5-dimethylanilino)carbonyl]methyl]phenoxy]-2-methylcyclopentane carboxylic acid was significantly more active that (+)1-[4-[[(3,5-dimethylanilino)carbonyl]methyl]phenoxy]-2-methylcyclopentane carboxylic acid and equipotent to RSR13 and JP7. However, the whole blood results revealed that the more active isomer from both 1-[4-[[(3,5-dimethylanilino)carbonyl]methyl]phenoxy]-2-methylcyclopentane carboxylic acid and 2-[4-[[(3,5-dimethylanilino)carbonyl]methyl]phenoxy]-propionic acid was only slightly more active than the racemic mixture. This suggest that there are pharmacokinetic and/or bioavailability factors involved, possibly enantioselective plasma protein binding. Enantioselective plasma protein binding has been observed for several drugs including ibuprofen, warfarin, and propanolol where the enantiomers differ in their affinity for plasma proteins resulting in differing free fractions of the isomers.

Oxygen Equilibrium Studies

Hemoglobin Solution Studies

The effectors were prepared as 10 mM stock solutions in 100 mM NaCl bis-Tris buffer, pH 7.2. After the addition of an excess of $NaHCO_3$, the solution was warmed to 60° C. and stirred for several hours. The solutions were back titrated carefully to pH 7.2 at 25° C. prior to use. Oxygen equilibrium measurements were performed with the HEMOX-analyzer (TCS Medical products, Southampton, Pa.) using purified stripped human adult hemoglobin as described previously. 4 mL of buffer, 100 mM NaCl, 50 mM bis-Tris at pH 7.2, is added to a cuvette in the HEMOX, followed by 200 μL of the 10 mM effector stock solution. Hemoglobin is then added to achieve a final Hb concentration of 60–70 PM on heme basis. Catalase (20 μg/mL) and 50 mM EDTA were added to limit oxidation of the hemes. The solution was then fully oxygen-saturated using 95% carbogen gas mixture. The oxygen pressure was gradually decreased to record the curve continuously from the right to the left. The saturation of hemoglobin was determined spectrophotometrically with a dual wavelength spectrophotometer (577 nm and 586.2 nm). The solution was stirred constantly during the 45–60 min recordings. The $P_{50}$ and $n_{50}$ values were calculated by linear regression analysis from data points comprised between 40 and 60% oxygen saturation.

Whole Blood Studies

The whole blood samples were collected in heparinized tubes from healthy volunteers and stored over ice. The sodium salts of the compounds were prepared as described earlier. A 200 mM stock solution of the effector was prepared in DMSO. A 5.0 mM test solution was prepared from 50 μL of the 200 mM test solution and 1950 μL of whole blood. The blood samples were incubated in IL 237 tonometers (Instrumentation Laboratories, Inc. Lexington, Mass.) for approximately 10–12 min at 37° C. and equilibrated at three separate concentrations of $O_2$ (20%, 40%, and 60%). After equilibration at each concentration of $O_2$, a sample was removed via syringe and aspirated into a IL 1420 Automated Blood Gas Analyzer (Instrumentation Laboratories, Inc. Lexington, Mass.) and a IL 482 and IL 682 Co-oximeter (Instrumentation Laboratories, Inc. Lexington, Mass.) to determine the pH, $pCO_2$, $PO_2$ and the hemoglobin oxygen saturation values ($sO_2$), respectively. The measured values for $pO_2$ and $sO_2$ at each oxygen saturation level were then subjected to a non-linear regression analysis using the program Scientist (Micromath, Salt Lake City, Utah) to calculate the $P_{509}$ and Hill coefficient values.

Since the compounds contemplated by this invention are capable of allosterically modifying hemoglobin so that a low oxygen affinity 'T' state is favored (right shifting the equilibrium curve), these compounds will be useful in treating a variety of disease states in mammals including humans where tissues suffer from low oxygen tension, such as cancer and ischemia. As pointed out by Hirst et al. in *Radiat. Res.,* Vol. 112, (1987), pp. 164, decreasing the oxygen affinity of hemoglobin in circulating blood has been shown to be beneficial in the radiotherapy of tumors. The compounds may be administered to patients in whom the affinity of hemoglobin for oxygen is abnormally high. Particular conditions include certain hemoglobinopathies and certain respiratory distress syndromes including respiratory distress syndromes in new born infants aggravated by high fetal hemoglobin levels and when the availability of hemoglobin/oxygen to the tissues is decreased (e.g., in ischemic conditions such as peripheral vascular disease, coronary occlusion, cerebral vascular accidents, or tissue transplant). The compounds may also be used to inhibit platelet aggregation and may be used for antithrombotic purposes and wound healing. Topical application could be used for wound healing. In addition, the compounds may be used to treat low oxygen related disorders in the brain such as Alzheimer's disease, depression, and schizophrenia. It may be desirable to administer the compounds to a patient prior to and/or simultaneously with the transfusion of the treated whole blood or red blood cells in order to avoid substantial variations in the hemoglobin oxygen affinity due to dilution that occurs when the blood is administered.

The compounds can be added to whole blood or packed cells, preferably at the time of storage or at the time of transfusion in order to facilitate the dissociation of oxygen from hemoglobin and improve the oxygen delivering capability of the blood. Preferably, the compounds would be added in an amount of about 50 mg to 1 g per unit of blood (473 ml) or unit of packed cells (235 ml). When blood is stored, the hemoglobin in the blood tends to increase its affinity for oxygen by losing 2,3-diphosphoglycerides. As described above, the compounds of this invention are capable of reversing and/or preventing the functional abnormality of hemoglobin which is observed when whole blood or packed cells are stored. The compounds may be added to whole blood or red blood cell fractions in a closed system using an appropriate reservoir in which the compound is placed prior to storage or which is present in the anticoagulating solution in the blood collecting bag.

Administration to a patient can be achieved orally by intravenous or intraperitoneal injection, or rectally by suppository where the dose and the dosing regiment is varied according to individual sensitivity and the type of disease state being treated.

If the compounds are used for wound healing, the compounds could advantageously be applied topically directly to the wound area. In addition, the compounds can be mixed with blood external to a patient's body prior to and/or simultaneously with a transfusion. The compounds can be administered in the pure form or in a pharmaceutically acceptable formulation including suitable elixirs, binders, and the like or as pharmaceutically acceptable salts (lithium, soidum, potassium, ammonium, alkaline metals, etc.) or other derivatives (esters, ethers, etc.). It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Solid diluents and excipients include lactose starch, conventional disintegrating agents, coatings and the like.

The following Examples discuss particular uses and administration routes for the allosteric hemoglobine modifiers of this invention.

EXAMPLE 2

Radiation Oncology

Solid tumors, such as brain metastasis and lung cancers, are oxygen deficient masses. The allostcric effectors of this invention deliver more oxygen to tumors, which increases radical formation that increases tumor killing during radiation.

EXAMPLE 3

Hypothermia Limiting or Preventing Hypoxia Induced Irreversive Myocardial Damage The allosteric effectors increase the efficiency of oxygen delivery at low blood flow and low temperatures, thus having the ability to prevent myocardial damage.

EXAMPLE 4

Resuscitation from Hemorrhagic Shock

The allosteric effectors may decrease the number of red blood cells required for treating hemorrhagic shock by increasing their efficiency of oxygen delivery.

EXAMPLE 5

Wound Healing, Diabetic Ulcers, Chronic Leg Ulcers, Pressure Sores, Tissue Transplants Experiments have shown that the allosteric effectors delivery of oxygen to wound healing is irnportant. Damaged tissues heal faster when there is better blood flow and increased oxygen tension. In addition, by increasing oxygen delivery to wounded tissue, the allosteric: effectors may play a role in the destruction of infection causing bacteria.

EXAMPLE 6

Stroke

The allosteric effectors will be effective in delivenng oxygen to the brain, especially before complete occlusion and reperfusion injuries occur due to free radical formation.

EXAMPLE 7

Cardiovascular/Angina Applications

The allosteric effectors of this invention should be capable of increased oxygen delivery to blocked arteries and surrounding muscles and tissues, thus relieving the distress of angina attacks. The compounds may serve as antithrombolytic agents and decrease fibrinogen.

EXAMPLE 8

Alzeimer's Disease

One of the many symptoms of Alzheimer's disease is decreased flow of oxygen to the brain. The allosteric effectors concentrate in red blood cells which allows enhanced delivery of oxygen to all areas of the body, including the brain. Thus, the allosteric effectors of the present invention can be used to combat the symptom of decreased oxygen flow to the brain and the resulting deterioration of the brain.

EXAMPLE 9

Acute Respiratory Disease Syndrome (ARDS)

ARDS is characterized by interstitial and/or alveolar edema and hemorrhage as well as perivascular lung edema associated with hyaline membrane, proliferation of collagen fibers, and swollen epithelium with increased pinocytosis. The enhanced oxygen delivering capacity attributable to the allosteric effectors of this invention can be used in the treatment and prevention of ARDS by combatting lower than normal oxygen delivery to the lungs.

EXAMPLE 10

Use of Allosteric Effectors with Micelles or for Use with Underwater Exploration Micelles are synthetic lipophylic membrane like spheres that are being intensively investigated for in vivo administration of biological materials. Soya lecithin is a common agent used in creating micelles within a fluid. The micelles protect encapsulated drugs or biological materials from undesired metabolism, antibody detection, etc. Addition of the allosteric hemoglobin moditiers of this invention to micelles which encapsulate hemoglobin will increase the delivery of oxygen to tissues. Since the allosteric effectors of this invention concentrate in erythrocytes when administered in vivo in rats, incorporation of the allosteric effectors in a micelle which encapsulates hemoglobin allows the effector to remain securely within the micelle until it has been degraded. In addition, because of the increased delivery of oxygen attributed to the allosteric effectors of this invention, the allosteric effectors can be used to increase the dive time for underwater divers.

While the above description has discussed several compounds in detail, one of ordinary skill in the art will understand that the compounds of the present invention can be described by the following general formula:

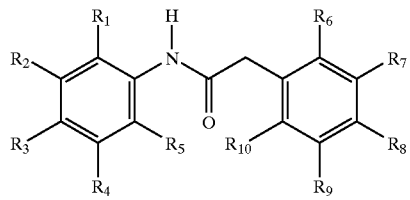

where
$R_1$–$R_{10}$ may be selected from the group consisting of $C_{1-6}$ alkyl, $C_{1-6}$ alkoxy, a carbon ring connecting any two of $R_1$–$R_5$, and a halogen; and at least one of $R_6$–$R_{10}$ is substituted with a moiety having the formula:

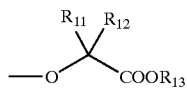

R$_{11}$ and R$_{12}$ may be part of a cyclic ring connecting R$_{11}$ and R$_{12}$ where the cyclic ring is selected from the group consisting of five member ring, alkyl substituted five member ring, six member ring, alkyl substituted six member ring, alkyl substituted heteroatom five member ring, heteroatom five member ring, and heteroatom six member ring. Further, R$_{11}$ and R$_{12}$ may be selected from the group consisting of C$_{1-5}$ alkyl, C$_{1-5}$ alkoxy, hydrogen, phenyl, aryl, and a halogen where R$_{11}$ and R$_{12}$ are different from one another.

R$_{13}$ may exist in its free acid form or may be in the form of a salt. Accordingly, R$_{13}$ selected from the group consisting of hydrogen, inorganic cation, organic cation, metal cation, and ammonium cation.

The compounds may be purified to provide either the positive (+) enantiomer or the negative (−) enantiomer.

Still further, one of R$_6$–R$_{10}$ may be-substituted with a moiety having the formula:

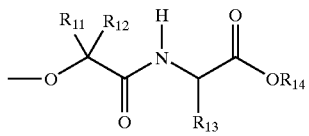

where R$_{11}$ and R$_{12}$ may be same or different from one another and are selected from the group consisting of C$_{1-5}$ alkyl, C$_{1-5}$ alkoxy, hydrogen, phenyl, aryl, and a cyclic ring connecting R$_{11}$ and R$_{12}$ where the cyclic ring is selected from the group consisting of five member ring, alkyl substituted five member ring, six member ring, alkyl substituted six member ring, alkyl substituted heteroatom five member ring, heteroatom five member ring, and heteroatom six member ring.

For these compounds R$_{13}$ may be selected from the group consisting of H, CH$_3$, CH(CH$_3$)$_2$, CH$_2$Ph, CH$_2$CH(CH$_3$)$_2$, CH(CH$_3$)C$_2$H$_5$, (CH$_2$)$_2$COOH, CH$_2$COOH, CH$_2$tryptophan, CH$_2$ Indole, CH$_2$PhOH, CH$_2$OH, CH$_2$SCH$_3$, (Me)$_2$SMe, (CH$_2$)$_3$, CH$_2$SCH$_2$Ph, CH(OH)CH$_3$, (CH$_2$)$_4$NHOCOCH$_2$Ph, and (CH$_2$)$_4$NH$_2$; and R$_{14}$ is selected from the group consisting of H and C$_{1-5}$ alkyl.

Still further, compounds of the present invention may have the following general formula:

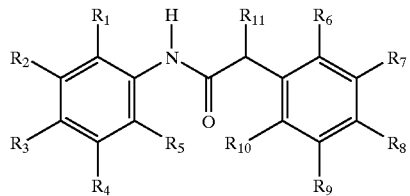

where R$_1$–R$_{10}$ are selected from the group consisting of C$_{1-6}$ alkyl, C$_{1-6}$ alkoxy, a carbon ring connecting any two of R$_1$–R$_5$ and a halogen; R$_{11}$ is selected from the group consisting of OH and C$_{1-5}$ alkoxy; and at least one of R$_6$–R$_{10}$ is substituted with a moiety having the formula:

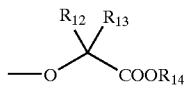

where R$_{12}$ and R$_{13}$ may be the same or different from one another and are selected from the group consisting of C$_{1-5}$ alkyl, C$_{1-5}$ alkoxy, hydrogen, phenyl, aryl, and a cyclic ring connecting R$_{12}$ and R$_{13}$ where the cyclic ring is selected from the group consisting of five member ring, alkyl substituted five member ring, six member ring, alkyl substituted six member ring, alkyl substituted heteroatom five member ring, heteroatom five member ring, and heteroatom six member ring; and R$_{14}$ is selected from the group consisting of hydrogen, inorganic cation, organic cation, metal cation, and ammonium cation.

Compounds of the present invention may also include compounds having the following general formula:

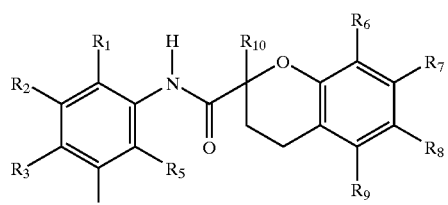

where R$_1$–R$_{10}$ are selected from the group consisting of C$_{1-6}$ alkyl, C$_{1-6}$ alkoxy, a carbon ring connecting any two of R$_1$–R$_5$, and a halogen; and at least one of R$_6$–R$_9$ is substituted with a moiety having the formula:

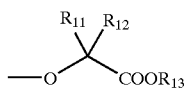

where R$_{11}$ and R$_{12}$ are selected from the group consisting of C$_{1-5}$ alkyl, C$_{1-5}$ alkoxy, hydrogen, phenyl, aryl, and a halogen; and R$_{13}$ is selected from the group consisting of hydrogen, inorganic cation, organic cation, metal cation, and ammonium cation.

Further, compounds of the present invention have broad utility such as described in U.S. Pat. Nos. 5,049,695; 5,122, 539; 5,248,785; 5,250,701; 5,290,803; 5,382,680; 5,432, 191; 5,525,630; 5,591,892; 5,648,375; 5,661,182; 5,667, 330; 5,705,521; 5,731,454; 5,827,888; U.S. patent application Ser. No. 08/848,485; United Kingdom Patent 0,471,811; French Patent 0,471,811; Italian Patent 0,471, 811; German Patent 691 15 790.1; Japanese Patent Applications 03–504,932 and 05–500,270; Canadian Patent Applicant 2,051,683 and 2,109,575; and European Patent Application 92 912 561.5 each of the above referenced patents and applications is herein incorporated by reference in their entirety.

While the invention has been described in terms of a single preferred embodiment, those skilled in the art will recognize that the invention can be practiced with modification within the spirit and scope of the appended claims.

What is claimed is:

1. A compound having the formula:

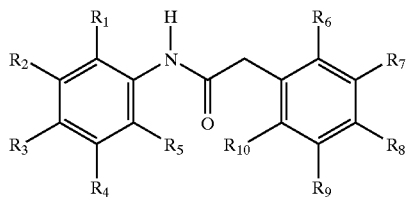

wherein:

$R_{1-10}$ are selected from the group consisting of hydrogen, $C_{1-6}$ alkyl, $C_{1-6}$ alkoxy, a carbon ring connecting any two of $R_1$–$R_5$, and a halogen; and at least one of $R_6$–$R_{10}$ is substituted with a moiety having the formula:

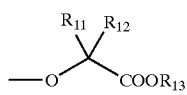

wherein:

$R_{11}$ and $R_{12}$ are part of a cyclic ring connecting $R_{11}$ and $R_{12}$ where the cyclic ring is selected from the group consisting of alkyl substituted five member ring, alkyl substituted six member ring, alkyl substituted heteroatom five member ring, and heteroatom six member ring; and $R_{13}$ is selected from the group consisting of hydrogen, inorganic cation, organic cation, metal cation, and ammonium cation.

2. The compound of claim 1 wherein $R_2$ and $R_3$ form a five member carbon ring connecting $R_2$ and $R_3$.

3. The compound of claim 1 wherein $R_2$ and $R_4$ are selected from the group consisting of chlorine and methyl.

4. The compound of claim 1 wherein $R_{11}$ and $R_{12}$ form a methyl substituted five member carbon ring.

5. The compound of claim 1 wherein $R_{11}$ and $R_{12}$ form a methyl substituted six member carbon ring.

6. The compound of claim 1 wherein $R_{11}$ and $R_{12}$ form a methyl substituted ring where the ring comprises carbon and oxygen.

7. The compound of claim 1 wherein $R_{11}$ and $R_{12}$ form a ring comprises carbon and oxygen.

8. A purified negative isomer having the formula:

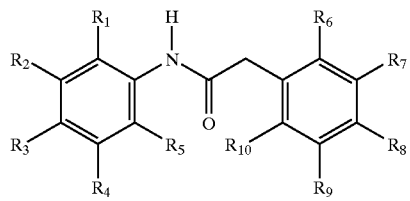

wherein:

$R_{1-10}$ are selected from the group consisting of hydrogen, $C_{1-6}$ alkyl, $C_{1-6}$ alkoxy, a carbon ring connecting any two of $R_1$–$R_5$, and a halogen; and at least one of $R_6$–$R_{10}$ is substituted with a moiety having the formula:

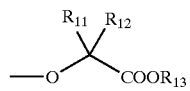

$R_{11}$ and $R_{12}$ are part of a cyclic ring connecting $R_{11}$ and $R_{12}$ where the cyclic ring is selected from the group consisting of five member ring, alkyl substituted five member ring, six member ring, alkyl substituted six member ring, alkyl substituted heteroatom five member ring, heteroatom five member ring, and heteroatom six member ring; and $R_{13}$ is selected from the group consisting of hydrogen, inorganic cation, organic cation, metal cation, and ammonium cation.

9. The compound of claim 8 wherein $R_2$ and $R_3$ form a five member carbon ring connecting $R_2$ and $R_3$.

10. The compound of claim 8 wherein $R_2$ and $R_4$ are selected from the group consisting of chlorine and methyl.

11. The compound of claim 8 wherein $R_{11}$ and $R_{12}$ form a methyl substituted five member carbon ring.

12. The compound of claim 8 wherein $R_{11}$ and $R_{12}$ form a methyl substituted six member carbon ring.

13. The compound of claim 8 wherein $R_{11}$ and $R_{12}$ form a methyl substituted ring where the ring comprises carbon and oxygen.

14. The compound of claim 8 wherein $R_{11}$ and $R_{12}$ form a ring comprising carbon and oxygen.

15. The compound of claim 8 wherein $R_{11}$ and $R_{12}$ form a five member carbon ring.

16. The compound of claim 8 wherein $R_{11}$ and $R_{12}$ form a six member carbon ring.

* * * * *